United States Patent
Paulus et al.

(10) Patent No.: US 9,321,012 B2
(45) Date of Patent: Apr. 26, 2016

(54) ELECTRONIC PROTEIN FRACTIONATION

(71) Applicants: Bio-Rad Laboratories, Inc., Hercules, CA (US); Technion Research & Development Foundation Ltd., Technion, Haifa (IL)

(72) Inventors: Aran Paulus, San Jose, CA (US); Roumen Bogoev, Hercules, CA (US); Elad Brod, Tivon (IL); Uri Sivan, Haifa (IL)

(73) Assignee: Bio-Rad Laboratories, Inc., Hercules, CA (US)

(*) Notice: Subject to any disclaimer, the term of this patent is extended or adjusted under 35 U.S.C. 154(b) by 489 days.

(21) Appl. No.: 13/803,564

(22) Filed: Mar. 14, 2013

(65) Prior Publication Data

US 2013/0277219 A1    Oct. 24, 2013

Related U.S. Application Data

(60) Provisional application No. 61/620,245, filed on Apr. 4, 2012.

(51) Int. Cl.
| | |
|---|---|
| *G01N 27/453* | (2006.01) |
| *B01D 61/54* | (2006.01) |
| *B01D 61/46* | (2006.01) |
| *B01D 61/44* | (2006.01) |
| *B01D 61/42* | (2006.01) |
| *C07K 1/28* | (2006.01) |
| *G01N 27/447* | (2006.01) |

(52) U.S. Cl.
CPC ............... *B01D 61/54* (2013.01); *B01D 61/42* (2013.01); *B01D 61/445* (2013.01); *B01D 61/46* (2013.01); *C07K 1/28* (2013.01); *B01D 2311/18* (2013.01); *G01N 27/44795* (2013.01)

(58) Field of Classification Search
CPC ............................. G01N 27/44795; C07K 1/28
See application file for complete search history.

(56) References Cited

U.S. PATENT DOCUMENTS

| | | | |
|---|---|---|---|
| 4,396,477 A | 8/1983 | Jain | |
| 4,868,130 A | 9/1989 | Hargreaves | |
| 4,880,513 A | 11/1989 | Davis et al. | |
| 4,900,414 A | 2/1990 | Sibalis | |
| 4,936,962 A | 6/1990 | Hatzidimitriu | |
| 5,045,204 A | 9/1991 | Dasgupta et al. | |
| 5,078,853 A * | 1/1992 | Manning et al. | 204/616 |
| 5,082,548 A | 1/1992 | Faupel et al. | |
| 5,160,594 A | 11/1992 | Huff et al. | |
| 5,198,086 A | 3/1993 | Chlanda et al. | |
| 5,437,774 A | 8/1995 | Laustsen et al. | |

(Continued)

FOREIGN PATENT DOCUMENTS

| | | |
|---|---|---|
| CN | 102079781 A | 6/2011 |
| EP | 0 979 868 A2 | 2/2000 |

(Continued)

OTHER PUBLICATIONS

U.S. Appl. No. 14/468,730, filed Aug. 26, 2014 (108 pages).

(Continued)

*Primary Examiner* — Alexander Noguerola
(74) *Attorney, Agent, or Firm* — Kilpatrick Townsend & Stockton LLP

(57) ABSTRACT

Apparatuses and methods for purifying proteins and other target molecules based on pI are provided.

23 Claims, 12 Drawing Sheets

(56) References Cited

U.S. PATENT DOCUMENTS

| | | | |
|---|---|---|---|
| 5,567,293 | A | 10/1996 | Paleologou et al. |
| 5,646,001 | A | 7/1997 | Terstappen et al. |
| 5,650,055 | A | 7/1997 | Margolis |
| 5,773,645 | A | 6/1998 | Hochstrasser |
| 6,077,434 | A | 6/2000 | Srinivasan et al. |
| 6,084,091 | A | 7/2000 | Muller et al. |
| 6,129,832 | A | 10/2000 | Fuhr et al. |
| 6,225,129 | B1 | 5/2001 | Liu et al. |
| 6,660,150 | B2 | 12/2003 | Conlan et al. |
| 6,969,453 | B2 | 11/2005 | Ogle et al. |
| 6,969,614 | B1 | 11/2005 | Liotta et al. |
| 7,077,942 | B1 | 7/2006 | Conlan et al. |
| 7,390,389 | B2 | 6/2008 | Rossier et al. |
| 7,517,696 | B2 | 4/2009 | Srinivasan et al. |
| 7,615,354 | B2 | 11/2009 | Faupel et al. |
| 7,651,838 | B2 | 1/2010 | Paterlini-Brechot |
| 7,989,614 | B2 | 8/2011 | Deggerdal et al. |
| 8,293,095 | B2 | 10/2012 | Han et al. |
| 2002/0043462 | A1 | 4/2002 | Ivory et al. |
| 2003/0083823 | A1 | 5/2003 | Parekh et al. |
| 2003/0168576 | A1 | 9/2003 | Panattoni et al. |
| 2003/0205471 | A1 | 11/2003 | Speicher et al. |
| 2003/0206894 | A1 | 11/2003 | De Boer et al. |
| 2003/0226752 | A1 | 12/2003 | Vigh |
| 2004/0242849 | A1 | 12/2004 | Rylatt et al. |
| 2005/0087445 | A1 | 4/2005 | Speicher et al. |
| 2006/0029978 | A1 | 2/2006 | O'Neill et al. |
| 2006/0037860 | A1 | 2/2006 | Ogle et al. |
| 2007/0163884 | A1 | 7/2007 | Strand et al. |
| 2007/0205106 | A1 | 9/2007 | Vigh et al. |
| 2008/0035484 | A1 | 2/2008 | Wu et al. |
| 2009/0101491 | A1 | 4/2009 | Bukshpan |
| 2009/0145777 | A1 | 6/2009 | Srinivasan |
| 2010/0155243 | A1 | 6/2010 | Schneider et al. |
| 2010/0307920 | A1 | 12/2010 | Sivan et al. |
| 2011/0195527 | A1 | 8/2011 | O'Neill et al. |
| 2012/0138468 | A1 | 6/2012 | Sivan et al. |
| 2012/0145548 | A1 | 6/2012 | Sivan et al. |

FOREIGN PATENT DOCUMENTS

| | | |
|---|---|---|
| EP | 1456667 B1 | 9/2004 |
| EP | 1748340 A2 | 1/2007 |
| WO | WO 99/26724 A2 | 6/1999 |
| WO | WO 01/36449 A1 | 5/2001 |
| WO | 03/019172 A2 | 3/2003 |
| WO | WO 2004/083405 A2 | 9/2004 |
| WO | 2006/063625 A1 | 6/2006 |
| WO | 2007/051492 A1 | 5/2007 |
| WO | WO 2009/027970 A2 | 3/2009 |
| WO | 2009/133153 A1 | 11/2009 |
| WO | 2010/048173 A2 | 4/2010 |
| WO | WO 2010/118890 A1 | 10/2010 |
| WO | WO 2011/021195 A2 | 2/2011 |
| WO | WO 2011/021196 A2 | 2/2011 |

OTHER PUBLICATIONS

Supplementary European Search Report dated Apr. 15, 2015 for EP Application No. 12845192.9, 6 pages.
Hughes et al., "Microfluidic integration for automated targeted proteomic assays", *Proceeding of the National Academy of Sciences*, 109(16):5972-5977 (2012).
Knittle et al., "Laser-induced flurescence detector for capillary-based isoelectric immunoblot assay", *Analytical Chemistry*, 79(24): 9478-9483.
O'Neill et al., "Isoelectric focusing technology quantifies protein signaling in 25 cells", *Proceedings of the National Academy of Sciences, National Academy of Sciences*, 103(44): 16153-16158 (2006).
Shimura et al., "Affinity Probe Capillary Electrophoresis: Analysis of Recombinant Human Growth Hormone with a Fluorescent Labeled Antibody Fragment", *Analytical Chemistry*, 66(1): 9-15 (1994).
Office Action from U.S. Appl. No. 13/669,012, mailed May 4, 2015, 22 pages.
Lu et al., "A Microfabricated Device for Subcellular Organelle Sorting", *Anal. Chem.*, 76:5705-5712 (2004).
Munce et al., "Microfabricated System for Parallel Single-Cell Capillary Electrophoresis", *Anal. Chem*, 76:4983-4989 (2004).
Pospichal et al., "Micropreparative Focusing of Proteins in Carrier-Ampholyte-free Solultion with Electrically Controlled Composition of Electrolytes", *J. Microcolumn Separations*, 7(3): 213-219 (1995).
Prochakova et al., "The use of Carrier Amphyolyte-Free Solelectric Focusing for Proteomic Analysis", *Chromatographia Supplement*, 67:S55-61 (2008).
Zhan et al., "Development of a simple amopholyte-free isoelectric focusing slab electrophoresis for protein fractionation", *Journal of Chromotograph A*, 1216:2929-2933 (2009).
The International Search Report and Written Opinion from PCT/US2012/063571, dated Feb. 20, 2013 (14 pages).
The International Search Report and Written Opinion from PCT/US2013/032906, dated Jun. 14, 2013 (9 pages).
The International Search Report and Written Opinion from PCT/US2012/063601, dated Feb. 15, 2013 (12 pages).
The International Search Report and Written Opinion from PCT/US2013/026485, dated Apr. 19, 2013 (14 pages).
The International Search Report and Written Opinion from PCT/US2012/063502, dated Jan. 22, 2013 (13 pages).
U.S. Appl. No. 13/668,651, filed Nov. 5, 2012 (43 pages).
U.S. Appl. No. 13/669,023, filed Nov. 5, 2012 (69 pages).
U.S. Appl. No. 13/669,012, filed Nov. 5, 2012 (42 pages).
U.S. Appl. No. 13/768,253, filed Feb. 15, 2013 (90 pages).
"Adjusting acidity with impunity." PHYSorq.com. Dec. 22, 2009. Retrieved at physorg.com/news180726696.html (author unknown).
"Isoelectric Focusing" from *European Pharmacopoeia Edition* 5.0, Chapter 2 "Methods of Analysis", Section 2.2.54 (p. 81-82). Published by the Council of Europe, Jun. 15, 2004.
"Isoelectric Focusing," *AES Application Focus* adapted from Chapter 7, Gel Electrophoresis of Proteins By David E. Garfin, pp. 197-268 in *Essential Cell Biology*, vol. 1: Cell Structure, A Practical Approach edited by John Davey and Mike Lord, Oxford University Press, Oxford UK (2003).
Ameridia, "Bipolar Membrane Electrodialysis—Applications of Bipolar Membrane Electrodialysis"; retrieved online at ameridia.com/htm/eba.html Jul. 12, 2011.
Ameridia, "Bipolar Membrane Electrodialysis—Process Description"; retrieved online at ameridia.com/htm/ebp.html Jul. 12, 2011.
Ameridia, "Bipolar Membrane Electrodialysis—Production of Organic or Amino Acids by Bipolar Membrane Electrodialysis"; retrieved online at ameridia.com/htm/ebc.html Jul. 12, 2011.
Amersham Pharmacia Biotech, "Hoefer IsoPrime IEF Purification Unit," User Manual (47 pages), 1999.
Bazinet et al.; "Bipolar Membrane Electroacidification To Produce Bovine Milk Casein Isolate"; *J. Agric. Food Chem.*: 47:5291-5296 (1999).
Bazinet et al.; "Effect of KCl and Soy Protein Concentrations on the Performance of Bipolar Membrane Electroacidification"; *J. Agric. Food Chem.*: 45:2419-2425 (1997).
Bazinet et al.; "Effect of Number of Bipolar Membranes and Temperature on the Performance of Bipolar Membrane Electroacidification"; *J. Agric. Food Chem.*; 45:3788-3794 (1997).
Biotech Daily, "Daily news on ASX-listed biotechnology companies," 4 pages, Oct. 10, 2008.
CAO, Liming (2005) *Protein Separation with Ion-exchange Membrane Chromatography*. (Master's Thesis) Retrieved online at wpi.edu/Pubs/ETD/Available/etd-050405-174109/.
Chen et al.; "Electrodialytic Membrane Suppressors for Ion Chromatography Make Programmable Buffer Generators"; *Anal. Chem.*; 84:67-75 (2012) ePub Nov. 21, 2011.
Chen et al.; "pH- and Concentration-Programmable Electrodialytic Buffer Generator"; *Anal. Chem.*; 84:59-66(2012) ePub Dec. 12, 2011.
Cheng et al.; "High-performance protein separation by ion exchange membrane partitioned free-flowisoelectric focusing system"; *Chem. Eng. Sci.*; 63:2241-2251 (2008).

(56) References Cited

OTHER PUBLICATIONS

Cheng et al.; "Micro-pH Control By Breaking Water And Its Applications". 15th International Conference on Miniaturized Systems for Chemistry and Life Sciences. Oct. 2-6, 2011, Seattle, Washington, USA (3 pages).
Cheng et al.; "Microscale pH Regulation by Breaking Water"; *Biomicrofluidics*; vol. 5, 046502, published online Nov. 2, 2011 (8 pages).
Cretich et al.; "Electroosmotic flow suppression in capillary electrophoresis: Chemisorption of trimethoxy silane-modified polydimethylacrylamide"; *Electrophoresis*; 26:1913-1919 (2005).
Das et al.; "Effects of separation length and voltage on isoelectric focusing in a plastic microfluidic device"; *Electrophoresis*; 27:3619-3626 (2006).
Denver Instrument, "Titration—Coulometric Karl Fischer Titration" brochure. (n.d.).
Dionex Corporation, "Eluent Suppressors for Ion Chromatography," Data Sheet (24 pages), 2010.
DKK-TOA Corporation, "AUT-701 Automatic Titrator" brochure. Jan. 10, 2008.
Douglas Instruments, "Oryx8" brochure. (n.d.).
Gregor, H.; "Ion-Exchange Membranes—Correlation Between Structure And Function"; *Pure Appl. Chem.*; 16(2-3)329-350 (1968).
Horvath et al.; "Multifunctional apparatus for electrokinetic processing of proteins"; *Electrophoresis*; 15:968-971 (1994).
Huang et al.; "Application of electrodialysis to the production of organic acids: State-of-the-art and recent developments"; *J. Membr. Sci.*; 288:1-12 (2007) ePub Nov. 25, 2006.
Huang et al.; "Capillary Isoelectric Focusing without Carrier Ampholytes" *Anal. Chem.*: 72:4758-4761.
Huang et al.; "Digitally Controlled Electrophoretic Focusing"; *Anal. Chem.*; 71(8):1628-1632 (1999) ePub Mar. 9, 1999.
Huang et al.; "The transitional isoelectric focusing process"; *Anal. Bioanal. Chem.*; 382:783-788 (2005).
Ivory, C.F.; "A Brief Review of Alternative Electrofocusing Techniques"; *Separation Science and Technology*; 35(11):1777-1793 (2000).
Jong et al., "Membranes and microfluidics: a review"; Lab Chip; (6): 1125-1139 (2006).
Karaltay Scientific Instruments, "Laboratory electrochemical analytical instruments—Automatic potentiometric titrators." 5 pages. (n.d.).
Karimi et al.; "Electroosmotic flow through polymer electrolyte membranes in PEM fuel cells"; *Journal of Power Sources*; 140:1-11 (2005).
Kelly et al.; "Electric field gradient focusing"; *J. Sep. Sci.*; 28:1985-1993 (2005).
Kohlmann, F.J.; "What is pH and how is it measured?—A Technical Handbook for Industry"; Lit. No. G004. 24 pages. Hach Company (2003).
Lee et al.; "Polymer Electrolyte Membranes for Fuel Cells"; *J. Ind. Eng. Chem.*; 12(2):175-183 (2006).
Li et al.; "An electrokinetic bioreactor: using direct electric current for enhanced lactic acid fermentation and product recovery"; *Tetrahedron*; 60:655-661 (2004).
Lutin et al.; "Keep it natural ! Adjusting the pH of food products without chemical additives thanks to Bipolar Membrane Electrodialysis." Presented on May 15, 2007. NAMS 2007 Annual Meeting May 11-16, 2007, Orlando, Florida (3 pages).
Ly, Linda. (2008). *Development of Selective Electrophoresis for Proteins and Peptides within Proteomes.* (Doctoral Dissertation) Retrieved from web at http://www.unsworks.unsw.edu.au/primo_library/libweb/action/dlDisplay.do?vid=UNSWORKS&docId=unsworks_4279.
Mettler Toledo, "Compact Titrator G20" brochure. Sep. 2009.
Michél et al.; "Protein fractionation in a multicompartment device using Off-Gel™ isolectric focusing"; *Electrophoresis*; 24:3-11 (2003).
Montgomery et al.; "Dynamic Isoelectric Focusing for Proteomics"; *Anal. Chem.*; 78:6511-6518.

Nagasubramanian et al.; "Use of Bipolar Membranes for Generation of Acid and Base—An Engineering and Economic Analysis"; *J. Membr. Sci.*; 2:109-124 (1977).
Nguyen et al.; "A Water and Heat Management Model for Proton-Exchange-Membrane Fuel Cells"; J. Electrochem. Soc.; *J. Electrochem. Soc.*; 140(8):2178-2186 (Aug. 1993).
NuSep Press Release, "NuSep Increases Profit Forecast to $1m after it Acquires BioInquire and completes Placement at 30c"; 2009 (4 pages).
NuSep Press Release, "NuSep Investor Presentations"; 2009 (4 pages).
NuSep, "Desalting protein samples by electro-dialysis using the ProteomeSep MF10," Application Note NAN004 (2 pages), n.d.
NuSep, "ProteomeSep—MF10 Membrane Fractionation Instrument for protein separations," Operators Manual (22 pages), 2008.
NuSep, "Removal of urea from protein samples using the ProteomeSep MF10," Application Note NAN005 (2 pages), n.d.
NuSep, "Separation of protein based on isoelectric point using the NuSep MF10," Application Note NAN001, Insert PII-055v1.1 (2 pages), n.d.
NuSep, MF10 Brochure (8 pages), (2008).
NuSep. 2008 Annual Report. 64 pages.
Ogle et al.; "Preparative-scale isoelectric trapping separations using a modified Gradiflow unit"; *J. Chromatogr. A*; 979:155-161 (2002).
PC Cell GmbH, "PCCell Ed 64 0 04" brochure. (n.d.).
Pearson et al.; "Production of synthetic ampholytes for isolectric focusing." (1979). *Nebraska Game and Parks Commission—White Papers, Conference Presentations, & Manuscripts.* Paper 13. Retrived onling at digitalcommons.unl.edu/nebgamewhitepap/13.
Piruska et al.; "The autofluorescence of plastic materials and chips measured under laser irradiation"; *Lab Chip*; 5:1348-1354 (2005) ePub Nov. 1, 2005.
Pospíchal et al.; "Analytical aspects of carrier ampholyte-free isoelectric focusing"; *J. Chromatog. A*; 918:195-203 (2001).
Pospíchal et al.; "Electrically controlled electrofocusing of ampholytes between two zones of modified electrolyte with two different values of pH"; *J. Chromatog. A*; 638:179-186 (1993).
Pospíchal et al.; "Micropreparative Focusing of Proteins in Carrier-Ampholyte-free Solution with Electrically Controlled Compositions of Electrolytes"; *J. Microcolumn Separations*; 7(3):213-219 (1995).
Ramierz et al.; "Current-voltage curves of bipolar membranes"; *J. Appl. Phys.*, 72(1):259-264 (Jul. 1992).
Silvertand et al.; "Recent developments in capillary isoelectric focusing"; *J. Chromatog. A*; 1204:157-170 (2008).
Silvertand, Linda H.H. (2009) *Isoelectric Focusing: Sample Pretreatment—Separation—Hyphenation.* (Doctoral Dissertation) Retreived online at igitur-archive.library.uu.nl/dissertations/2010-0106-200200/UUindex.html.
Song et al.; "Fabrication and Characterization of Photpatterned Polymer Membranes for Protein Concentration and Dialysis in Microchips" in Hilton Head, South Carolina MEMS Workshop Jun. 6-10, 2004 (May 2004).
Standard Operating Procedure, "SOP for Gradiflow MF10 (prototype)," 6 pages, (2007).
TechniKrom, "New cGMP Bioprocessing Tool: Automated Rapid pH Adjustment Systems" brochure. (2006).
Thomas et al.; "Gradipore™—The Preparative Electrophoresis System, Gradiflow™"; Poster MB-04, 1 page, n.d.
Thomas et al.; "Preparative electrophoresis: a general method for the purification of polyclonal antibodies"; *J. Chromatogr. A*; 944:161-168 (2002).
Thomas et al.; Gradipore, "Comparison of Gradiflow and Affinity Chromatography Methods of Antibody Preparation," Gradipore Application Note AN3004 (Jul. 2003).
Thormann et al.; "High-resolution computer simulation of the dynamics of isoelectric focusing using carrier ampholytes: Focusing with concurrent electrophoretic mobilization is an isotachophoretic process"; *Electrophoresis*; 27:968-983 (2006).
Tongwen et al.; "Citric acid production by electrodialysis with bipolar membranes"; *Chemical Engineering and Processing*; 41:519-524 (2002).
Walter et al.; "Protein microarrays: Reduced autofluorescence and improved LOD"; *Eng. Life Sci.*; 10(2):103-108 (2010).

(56) References Cited

OTHER PUBLICATIONS

Wei et al.; "One-step concentration of analytes based on dynamic change in pH in capillary zone electrophoresis"; *Anal. Chem.*; 74:934-940 (2002).

Wei et al.; "On-line concentration of proteins and peptides in capillary zone electrophoresis with an etched porous joint"; *Anal. Chem.*; 74:3899-3905 (2002).

Wellhausen et al.; "Facing Current Qualification Challenges in ProteinMicroarrays"; *J. Biomed. Biotechnol.*; vol. 2012, Article ID 831347, 8 pages, ePub Apr. 24, 2012.

Westermeier et al.; "Protein Detection Methods in Proteomics Research"; *Bioscience Reports*; 25(1/2):19-32 (2005).

Wilhelm, Friedrich G. (2001) Bipolar Membrane Electrodialysis. (Doctoral Thesis) Retrieved online at tup.utwente.nl/uk/catalogue/technical/electrodialysis.

Wong et al.; "Application of bipolar electrodialysis to *E. coli* fermentation for simultaneous acetate removal and pH control"; Biotechnol. Lett.; 32:1053-1057 (2010) ePub Apr. 11, 2010.

Wong, Michael. (2011) *Application of electrodialysis in integrated microbial fermentation and enzymatic biotransformation processes.* (Doctoral Thesis) Retreived online at discovery.ucl.ac.uk/1310480/1/1310480.pdf.

Wu et al.; "Isoelectric focusing sample injection for capillary electrophoresis of proteins"; *Electrophoresis*; 26:563-570 (2005).

Xu et al.; "Development of bipolar membrane-based processes"; *Desalination*; 140:247-258 (2001).

Xu et al.; "Electrodialysis-Based Separation Technologies: A Critical Review"; *American Institute of Chemical Engineers Journal*; 54(12):3147-3159 (2008) ePub Oct. 2, 2008.

Xu et al.; "Ion exchange membranes: State of their development and perspective"; *J. Membr. Sci.*; 263:1-29 (2005).

Zhang et al.; "Isoelectric Focusing Sample Injection for Capillary Zone Electrophoresis in a Fused Silica Capillary"; *Analytical Sciences*; 22:1039-1041 (Jul. 2006).

Zuo et al.; "A Method for Global Analysis of Complex Proteomes Using Sample Prefractionation by Solution Isoelectrofocusing Prior to Two-Dimensional Electrophoresis"; *Anal. Biochem.*; 284:266-278.

Armstrong et al., "Separating Microbes in the Manner of Molecules. 1. Capillary Electrokinetic Approaches", *Anal. Chem*, 71: 5465-5469 (1999).

Cabrera et al., "Continous concentration of bacteria in a microfluidic flow cell using electrokinetic techniques", *Eletrophoresis*, 22:355-362 (2001).

The Extended European Search Report dated Sep. 18, 2015 for European Patent Application No. 12845686.0, 11 pages.

The Extended European Search Report dated Jun. 22, 2015 for European Patent Application No. 12844702.6, 7 pages.

\* cited by examiner

ELECTRONIC PROTEIN FRACTIONATION

CROSS-REFERENCE TO RELATED PATENT APPLICATIONS

The present patent application claims benefit of priority to U.S. Provisional patent application No. 61/620,245, filed Apr. 4, 2012, which is incorporated by reference for all purposes.

BACKGROUND OF THE INVENTION

Protein purification is desirable in many instances. However, often protein purification is tedious and time-consuming.

BRIEF SUMMARY OF THE INVENTION

Aspects of the invention are described throughout this document.

In some embodiments, an apparatus is provided. In some embodiments, the apparatus comprises:
a chamber divided into a first sub-chamber and a second sub-chamber by a dividing membrane,
wherein the dividing membrane blocks or substantially blocks flow of fluid between the first and second sub-chamber; and wherein
the first sub-chamber is in electrical communication with a first electrode;
the second sub-chamber is in electrical communication with a second electrode;
the first sub-chamber is in fluid communication with a first ion injector/extractor;
the second sub-chamber is in fluid communication with a second ion injector/extractor; and
and the second sub-chamber comprises an outlet.

In some embodiments, the first electrode is separated from the first sub-chamber by a first separation membrane and the second electrode is separated from the second sub-chamber by a second separation membrane, wherein the separation membranes are permeable to small ions but not larger molecules.

In some embodiments, the first ion injector/extractor comprises the first electrode and the second ion injector/extractor comprises the second electrode.

In some embodiments, the second sub-chamber is smaller than the first sub-chamber.

In some embodiments, the first electrode is an anode and the second electrode is a cathode. In some embodiments, the first electrode is a cathode and the second electrode is an anode.

In some embodiments, the injector/extractors are directly linked to the respective sub-chambers. In some embodiments, the injector/extractors are linked to the respective sub-chambers via tubing or a channel.

In some embodiments, the second sub-chamber further comprises one or more inlet. In some embodiments, the dividing membrane comprises a layer of cross-linked polymer, thereby inhibiting fluid diffusion. In some embodiments, the dividing membrane contains pores that allow passage of peptides smaller than a molecular cut-off but substantially block passage of peptides larger than the molecular cut-off. In some embodiments, the molecular cut-off is about 20 kDa.

In some embodiments, the ion injector/extractors each comprise:
a. a compartment in fluid communication with a sub-chamber and divided from the sub-chamber by an anion selective membrane; and/or
b. a compartment in fluid communication with the sub-chamber and divided from the sub-chamber by a bipolar membrane; and/or
c. compartment in fluid communication with a sub-chamber and divided from the sub-chamber by a cation selective membrane.

In some embodiments, the apparatus comprises:
a chamber divided into a first sub-chamber and a second sub-chamber by a dividing membrane,
wherein the dividing membrane blocks or substantially blocks flow of fluid between the first and second sub-chamber; and wherein
the first sub-chamber is in electrical communication with a first electrode separated from the first sub-chamber by a first separation membrane;
the second sub-chamber is in electrical communication with a second electrode separated from the second sub-chamber by a second separation membrane, wherein the separation membranes are permeable to small ions but not larger molecules;
the first sub-chamber is in fluid communication with a first proton/anion injector/extractor and a first hydroxide/cation injector/extractor;
the second sub-chamber is in fluid communication with a second proton/anion injector/extractor and a second hydroxide/cation injector/extractor; and
and the second sub-chamber comprises an outlet.

In some embodiments, the second sub-chamber is smaller than the first sub-chamber.

In some embodiments, the first electrode is an anode and the second electrode is a cathode. In some embodiments, the first electrode is a cathode and the second electrode is an anode.

In some embodiments, the injector/extractors are directly linked to the respective sub-chambers. In some embodiments, the injector/extractors are linked to the respective sub-chambers via tubing or a channel.

In some embodiments, the second sub-chamber further comprises one or more inlet.

In some embodiments, the dividing membrane comprises a layer of cross-linked polymer, thereby inhibiting fluid diffusion. In some embodiments, the dividing membrane contains pores that allow passage of peptides smaller than a molecular cut-off but substantially block passage of peptides larger than the molecular cut-off. In some embodiments, the molecular cut-off is about 10, 15, 20, 25, or 30 kDa, e.g., between 10-30 kDa.

In some embodiments, the proton/anion injector/extractors each comprise
a. a first compartment in fluid communication with a sub-chamber and divided from the sub-chamber by an anion selective membrane; and
b. a second compartment in fluid communication with the sub-chamber and divided from the sub-chamber by a bipolar membrane.

In some embodiments, the hydroxide/cation injector/extractors each comprise:
a. a third compartment in fluid communication with a sub-chamber and divided from the sub-chamber by a cation selective membrane; and
b. a fourth compartment in fluid communication with a sub-chamber and divided from the sub-chamber by a bipolar membrane.

Also provided are systems comprising the apparatus as described herein wired to a power supply, optionally further comprising a pump, UV detector, pH meter and/or conductivity meter.

Also provided are methods of purifying a target protein(s) or peptide(s) from a sample. In some embodiments, the method comprises
providing the apparatus as described above or elsewhere described herein;
loading the sample into the first sub-chamber, or the first and second sub-chambers, wherein the first and second sub-chambers contain fluid following the loading,
controlling the injector/extractors to adjust the pH of the fluid in the chamber to a pH such that some components of the sample are charged due to the pH adjustment and some components are not charged;
applying a voltage between the first and second electrode, thereby moving at least some charged components into the second sub-chamber; and
removing the fluid in the second chamber including the charged components via the outlet in the second sub-chamber, thereby separating the target protein(s) or peptide(s) in the sample from at least some other components of the sample.

In some embodiments, one or more target protein or peptide is a charged component moved to the second sub-chamber, and the target protein or peptide is collected after the removing.

In some embodiments, the charged components moved to the second sub-chamber are contaminants and discarding the contaminants.

In some embodiments, the sample is loaded into the first sub-chamber only.

In some embodiments, the sample is loaded into the first and second sub-chambers.

In some embodiments, the first electrode is a cathode (negative charge) and the second electrode is an anode (positive charge), and
the controlling comprises adjusting the pH of the fluid below the pI of the target protein(s) or peptide(s) such that the target protein(s) or peptide(s) have an overall positive charge and at least some other components of the sample are negatively-charged; and
the applying results in movement of the negatively-charged components to the second sub-chamber and the target protein(s) or peptide(s) remain in the first sub-chamber; and
removing fluid comprising the moved components from the second sub-chamber and optionally replacing the removed fluid with new fluid in the second sub-chamber; and subsequently
controlling the injector/extractors to adjust the pH of the fluid in the chamber to a pH above the pI of the target protein(s) or peptide(s) such that the target protein(s) or peptide(s) have an overall negative charge;
applying a voltage between the first and second electrode, thereby moving the negatively-charged target protein(s) or peptide(s) into the second sub-chamber; and
removing and collecting the fluid in the second chamber, including the target protein(s) or peptide(s), via the outlet in the second sub-chamber, thereby separating the target protein(s) or peptide(s) in the sample from at least some other components of the sample.

In some embodiments, the first electrode is an anode (positive charge) and the second electrode is a cathode (negative charge), and
the controlling comprises adjusting the pH of the fluid above the pI of the target protein(s) or peptide(s) such that the target protein(s) or peptide(s) have an overall negative charge and at least some other components of the sample are positively-charged; and
the applying results in movement of the positively-charged components to the second sub-chamber and the target protein(s) or peptide(s) remain in the first sub-chamber; and
removing fluid comprising the moved components from the second sub-chamber and optionally replacing the removed fluid with new fluid in the second sub-chamber; and subsequently
controlling the injector/extractors to adjust the pH of the fluid in the chamber to a pH below the pI of the target protein(s) or peptide(s) such that the target protein(s) or peptide(s) have an overall positive charge;
applying a voltage between the first and second electrode, thereby moving the positively-charged target protein(s) or peptide(s) into the second sub-chamber; and
removing and collecting the fluid in the second chamber, including the target protein(s) or peptide(s), via the outlet in the second sub-chamber, thereby separating the target protein(s) or peptide(s) in the sample from at least some other components of the sample.

In some embodiments, the sample comprises proteins and the dividing membrane contains pores that allow passage of peptides smaller than a molecular cut-off but that substantially block passage of peptides larger than the cut-off, and the loading comprises loading the sample into the first sub-chamber, optionally, the controlling comprises controlling the injector/extractors to adjust the pH of the fluid in the first sub-chamber;
adding a first protease to the first-sub chamber under conditions to allow the first protease to generate peptides from the proteins;
applying a voltage between the first and second electrode, thereby moving at least some charged peptides having a size below the molecular cut-off into the second sub-chamber.

In some embodiments, the molecular cut-off is about 10, 15, 20, 25, or 30 kDa, e.g., between 10-30 kDa.

In some embodiments, the method further comprises, adding a second protease to the first sub-chamber under conditions to allow the second protease to generate peptides from the proteins;
applying a voltage between the first and second electrode, thereby moving at least some charged peptides having a size below the molecular cut-off into the second sub-chamber.

In some embodiments, the method comprises, before or after adding the second protease, adjusting the pH of the fluid in the first sub-chamber to a pH optimized for the second protease.

In some embodiments, before the adding of the first protease, the method comprises applying a voltage between the first and second electrode, thereby moving at least some charged peptides, if present from the sample, into the second sub-chamber.

In some embodiments, the method further comprises collecting the peptides in the second sub-chamber.

Figure 1:
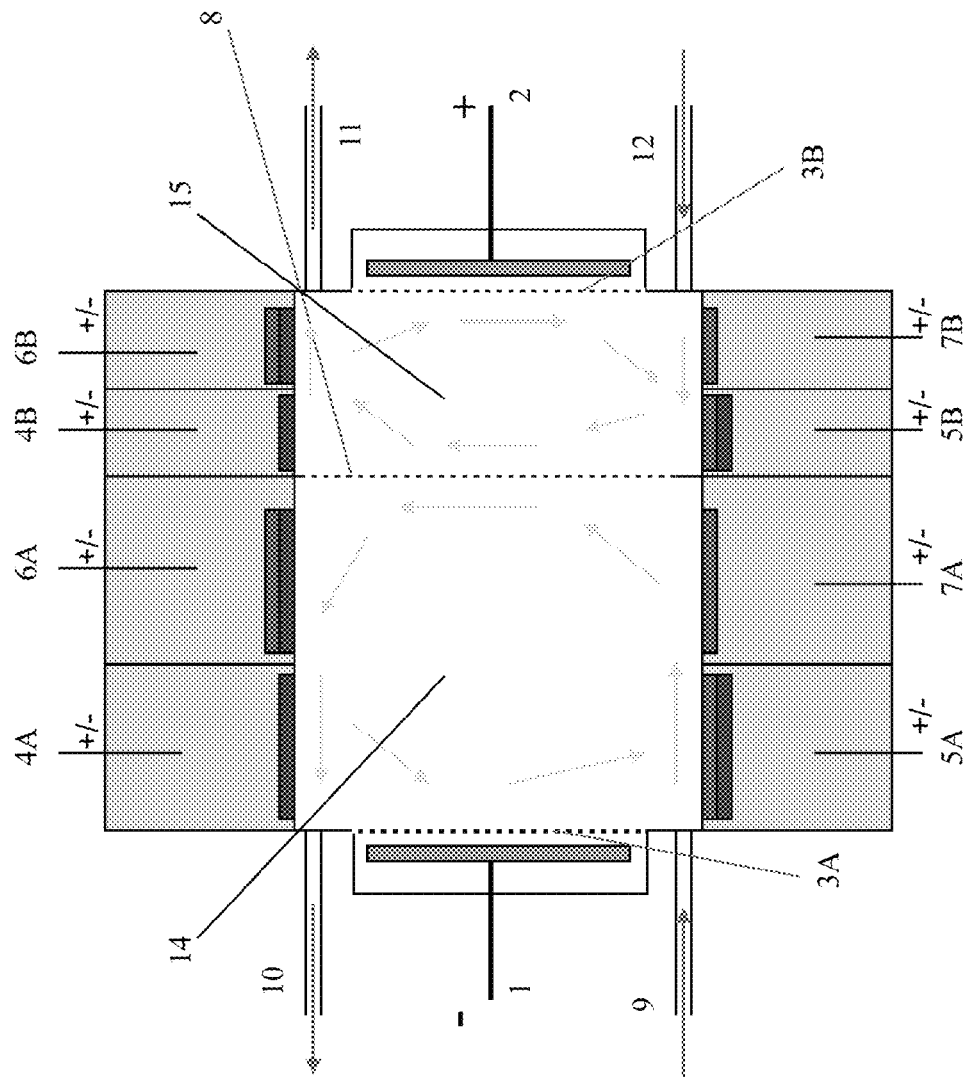
FIG. 1 illustrates an exemplary embodiment of an apparatus as described herein. A voltage applied between two electrodes (1 and 2) can move charged molecules towards the appropriate electrode (cathode or anode, depending on charge). The charged molecules can be moved, for example from the first sub-chamber (14) through the membrane (8) into the second sub-chamber (15). The pH of each sub-chamber can be regulated and changed using the ion injectors/extractors depicted as 4A, 5A, 6A, 7A, 4B, 5B, 6B, and 7B. Other membranes (3A and 3B) can protect the solution and components in the sub-chambers from the electrodes.

Optionally, the first sub-chamber (14) can include one or more outlet (10) and inlet (9). Similarly, the second sub-chamber (15) can include one or more outlet (11) and inlet (12).

Figure 2:
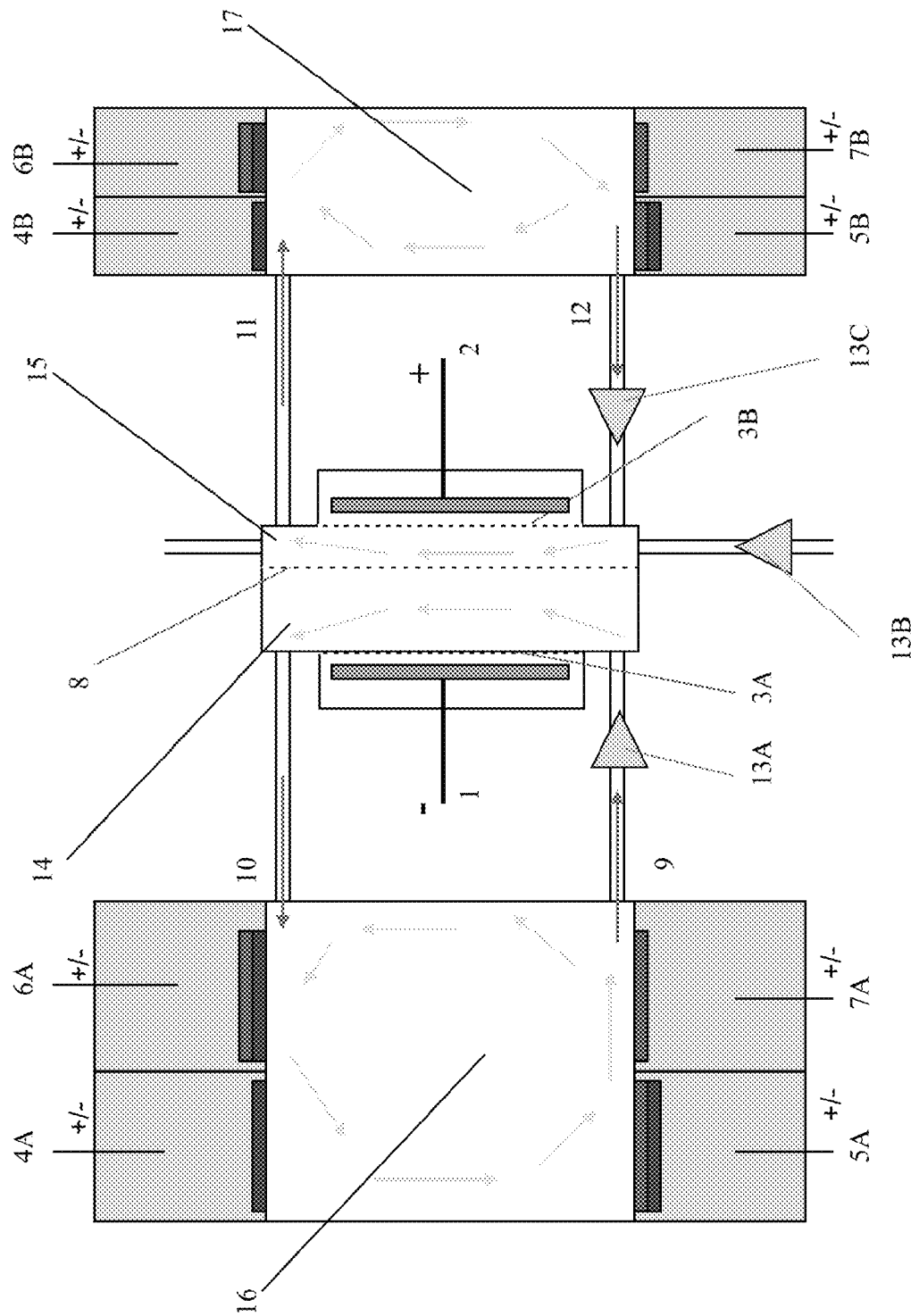

FIG. 2 illustrates an exemplary embodiment of an apparatus as described herein. A voltage applied between two electrodes (1 and 2) can move charged molecules towards the appropriate electrode (cathode or anode, depending on charge). The charged molecules can be moved, for example from the first sub-chamber (14) through the membrane (8) into the second sub-chamber (15). In this embodiment, the pH of solution in a reservoir (16 and 17) can be regulated and changed using the ion injectors/extractors depicted as 4A, 5A, 6A, 7A, 4B, 5B, 6B, and 7B. The solution can then be moved from reservoir (16) by inlet (9) into the first sub-chamber (14) and from reservoir (17) by inlet (12) into the second sub-chamber (15). A pump (13A and 13C) can move the solution, if desired. Outlets (10 and 11) can circulate the solution back to the reservoirs if desired. If desired, a pump (13B) can pump fresh solution from an external source. Other membranes (3A and 3B) can protect the solution and components in the sub-chambers from the electrodes.

Figure 3:
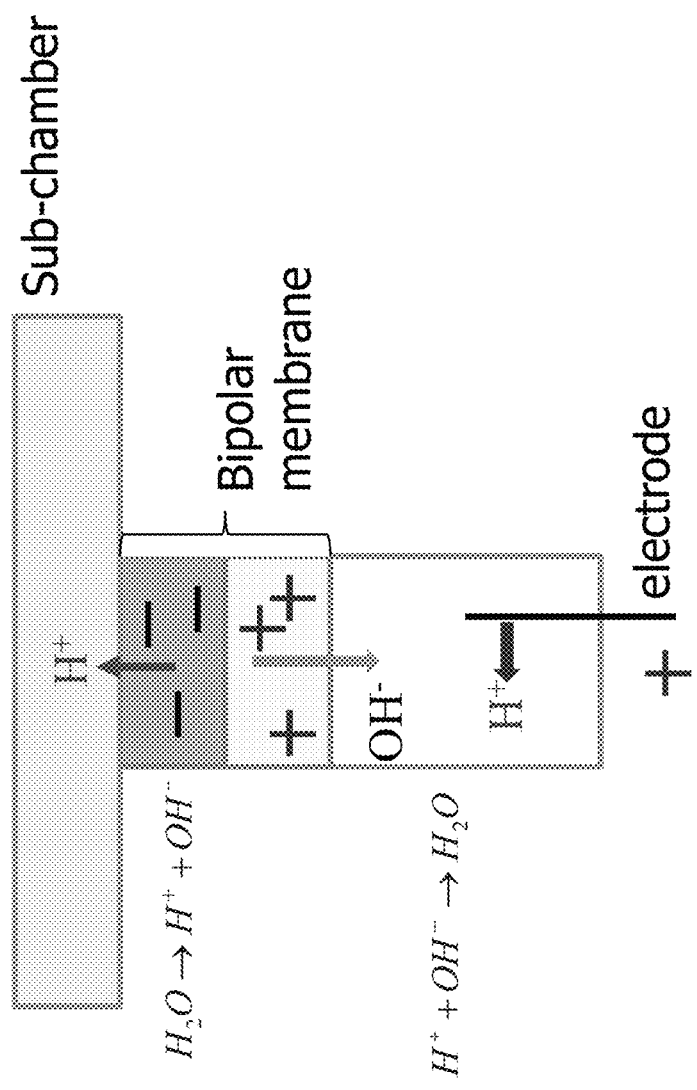

FIG. 3 illustrates a proton injector comprising a small compartment adjacent to the channel, with an electrode (e.g., a Pt electrode) dipped inside it, and a bipolar membrane separating the compartment from the channel. This figure is not intended to show the entire apparatus but merely shows how a proton injector can be attached to a sub-chamber.

Figure 4:
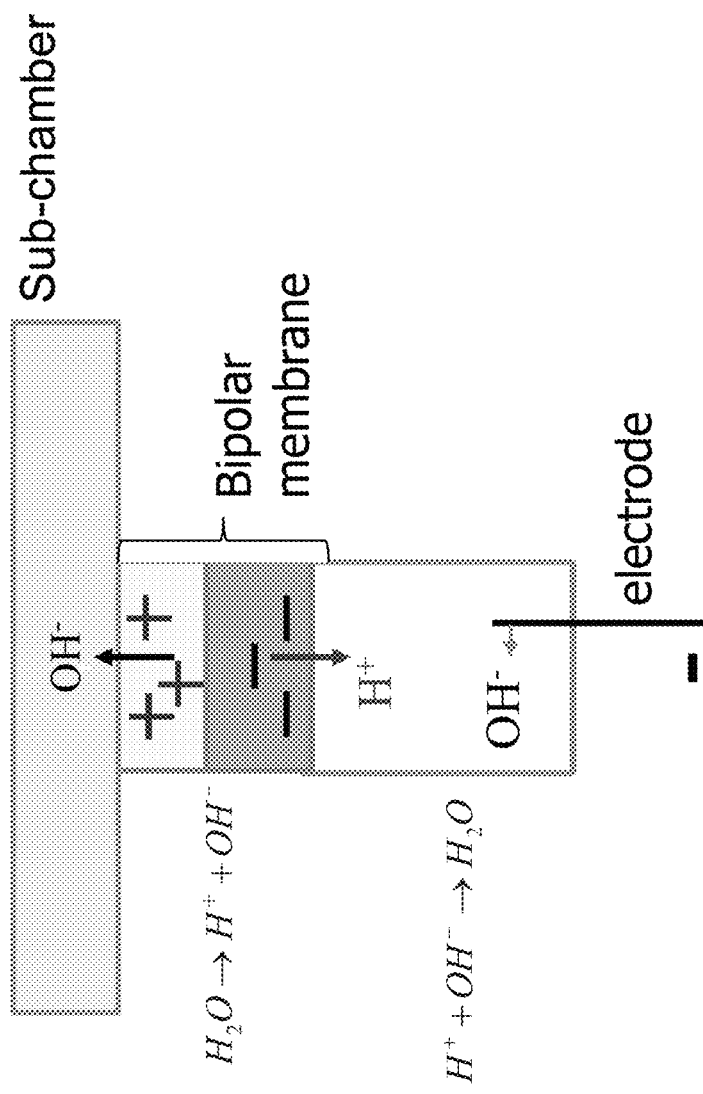

FIG. 4 illustrates a hydroxide injector comprising a small compartment adjacent to the channel, with an electrode (e.g., a Pt electrode) dipped inside it, and a bipolar membrane separating the compartment from the channel. This figure is not intended to show the entire apparatus but merely shows how a hydroxide injector can be attached to a sub-chamber.

Figure 5:
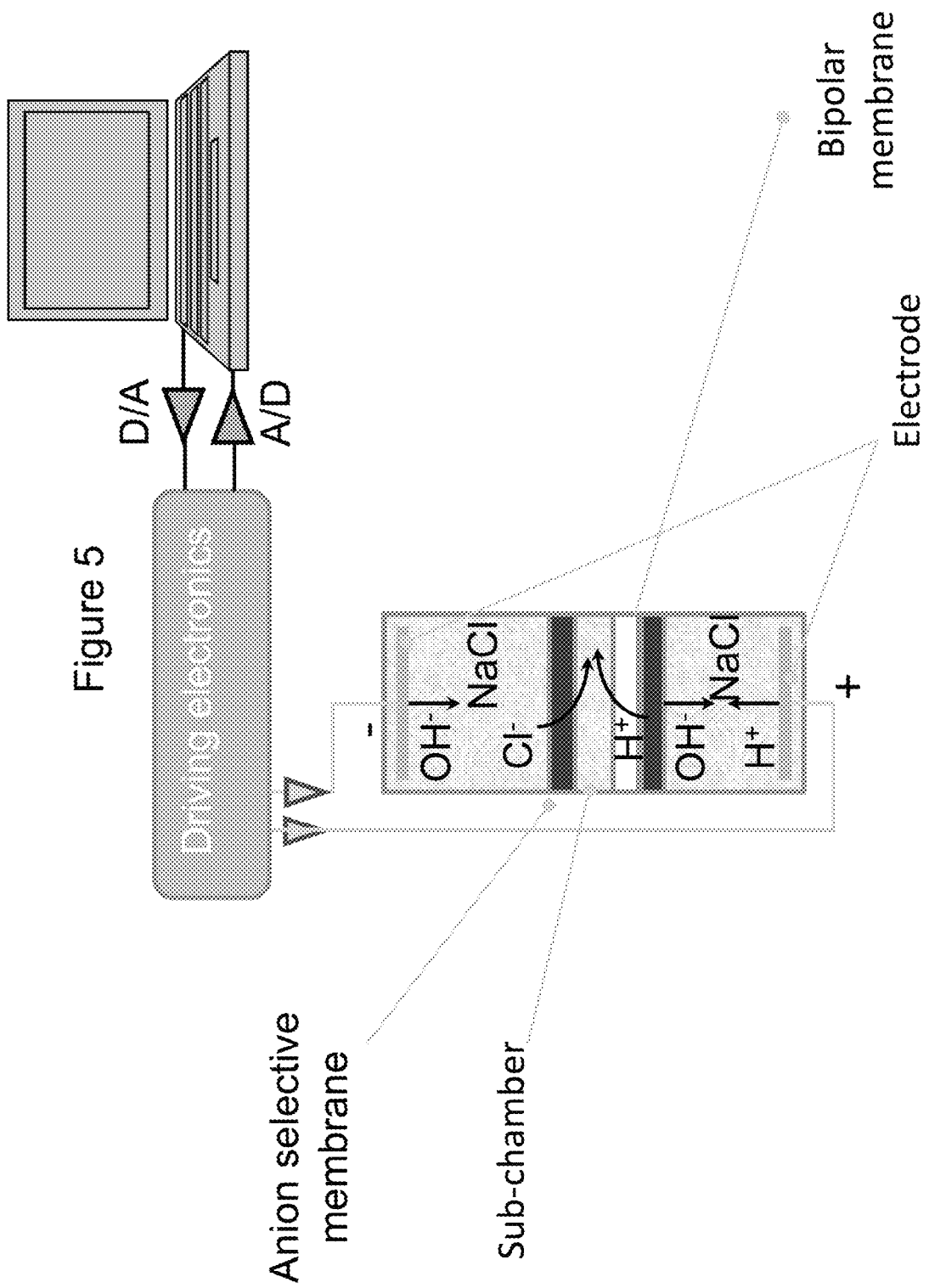

FIG. 5 depicts a compartment that injects anions (chloride ions depicted) and protons into a sub-chamber. This figure is not intended to show the entire apparatus but merely shows how a compartment can be attached to a sub-chamber.

Figure 6:
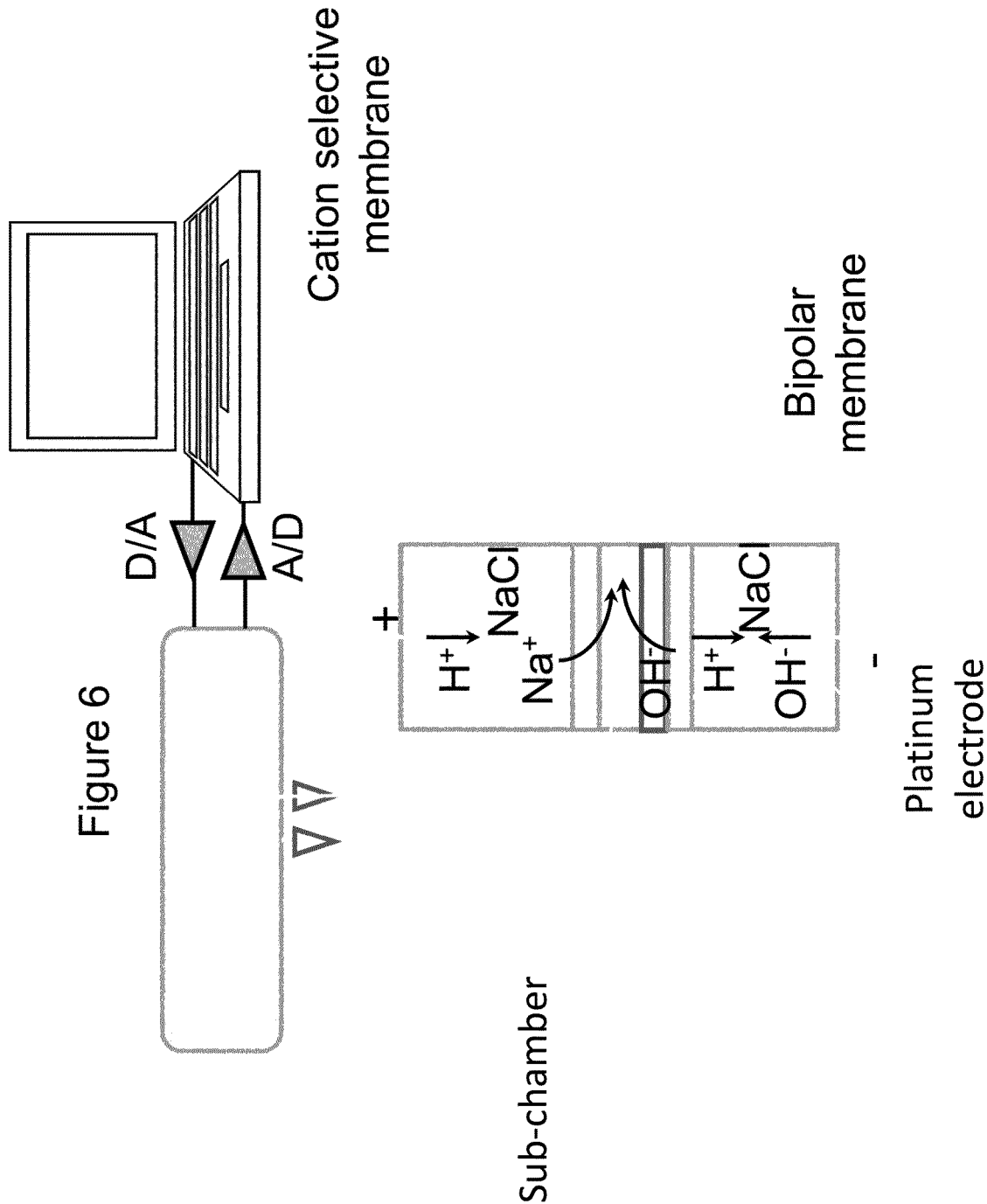

FIG. 6 depicts a compartment that injects cations (sodium ions depicted) and hydroxide ions into a sub-chamber. This figure is not intended to show the entire apparatus but merely shows how a compartment can be attached to a sub-chamber.

Figure 7:
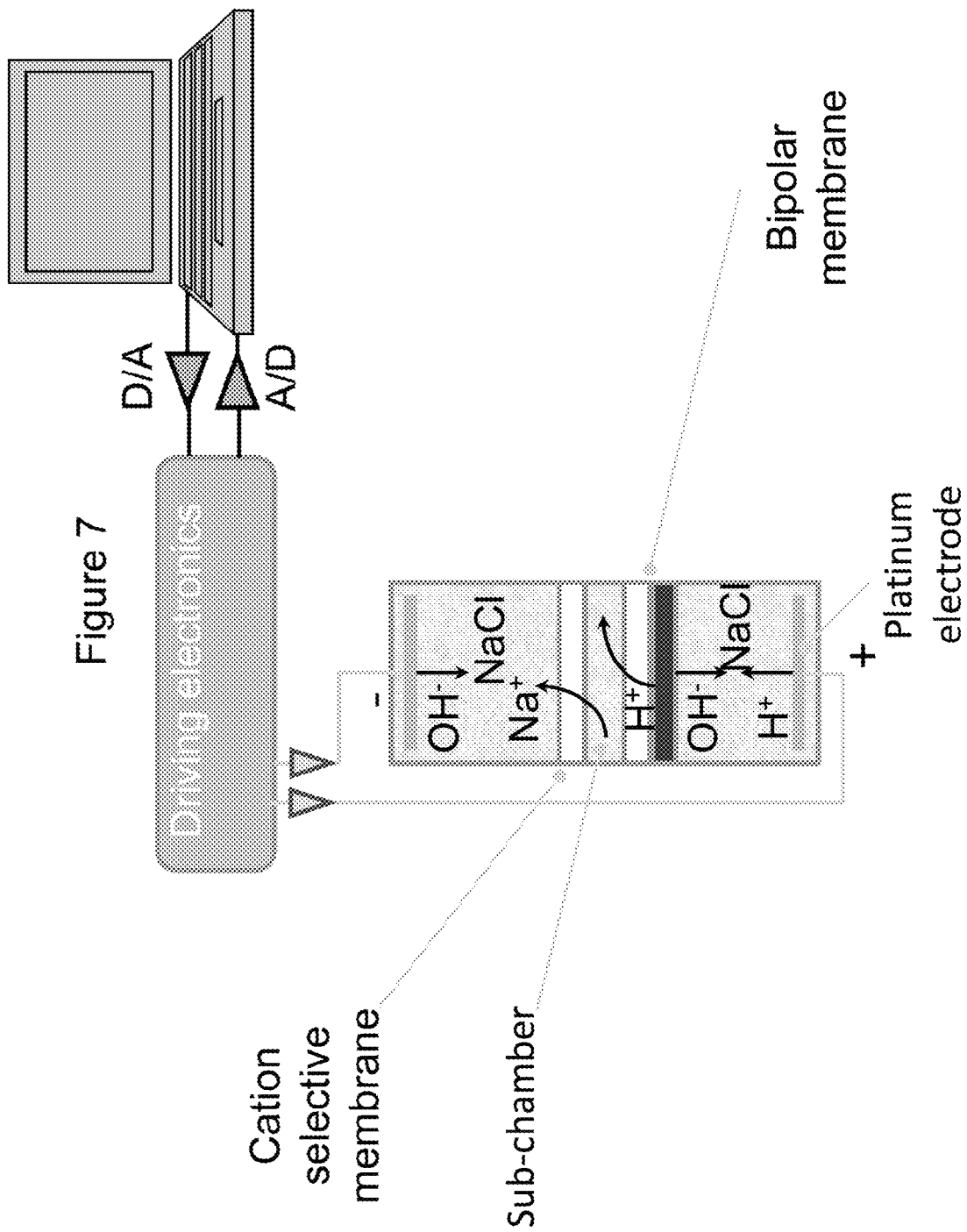

FIG. 7 depicts a compartment that injects protons into a sub-chamber while extracting cations (sodium ions depicted) from the sub-chamber. This figure is not intended to show the entire apparatus but merely shows how a compartment can be attached to a sub-chamber.

Figure 8:
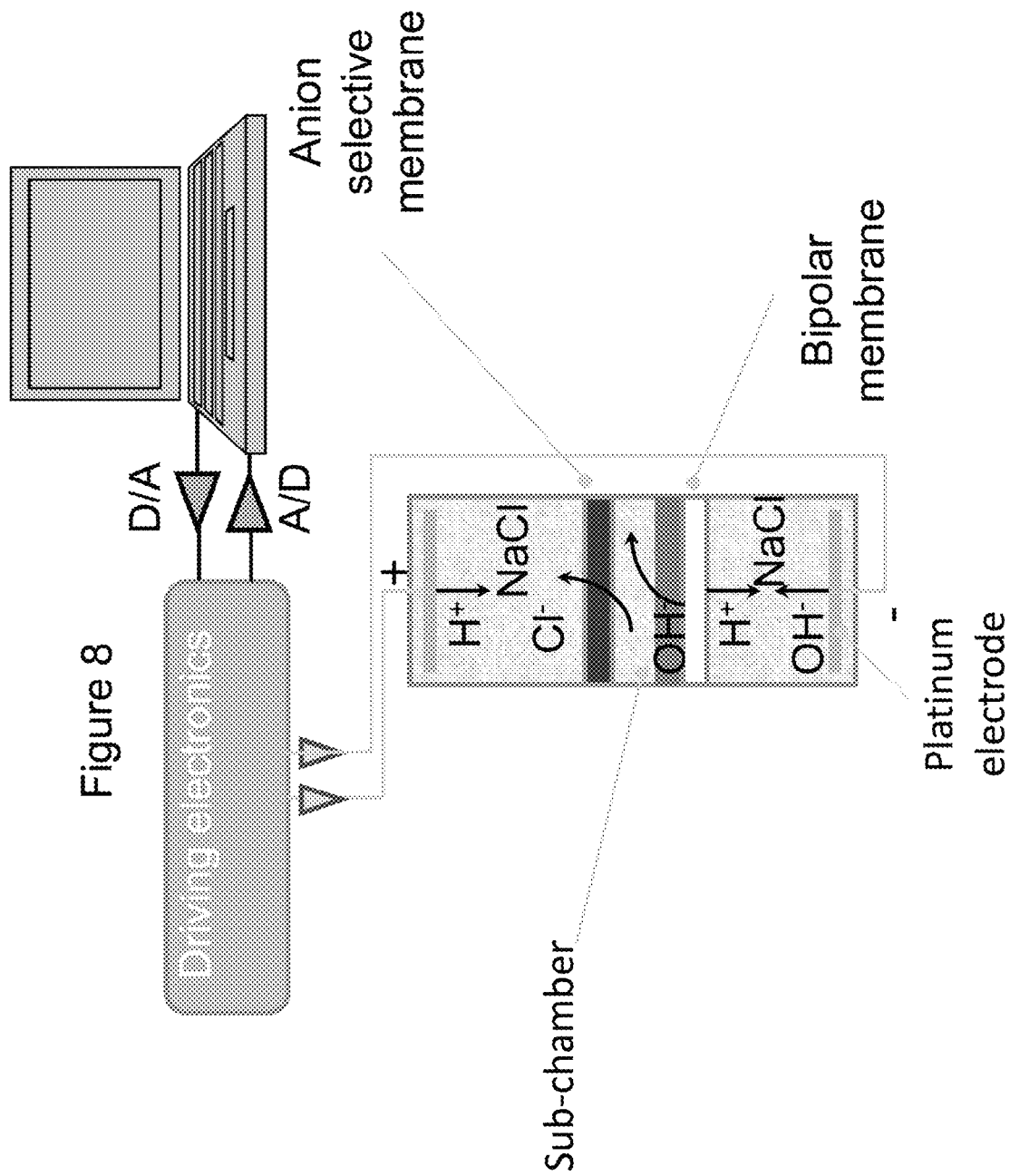

FIG. 8 depicts a compartment that injects hydroxide ions into a sub-chamber while extracting anions (chloride ions depicted) from the sub-chamber. This figure is not intended to show the entire apparatus but merely shows how a compartment can be attached to a sub-chamber.

Figure 9:
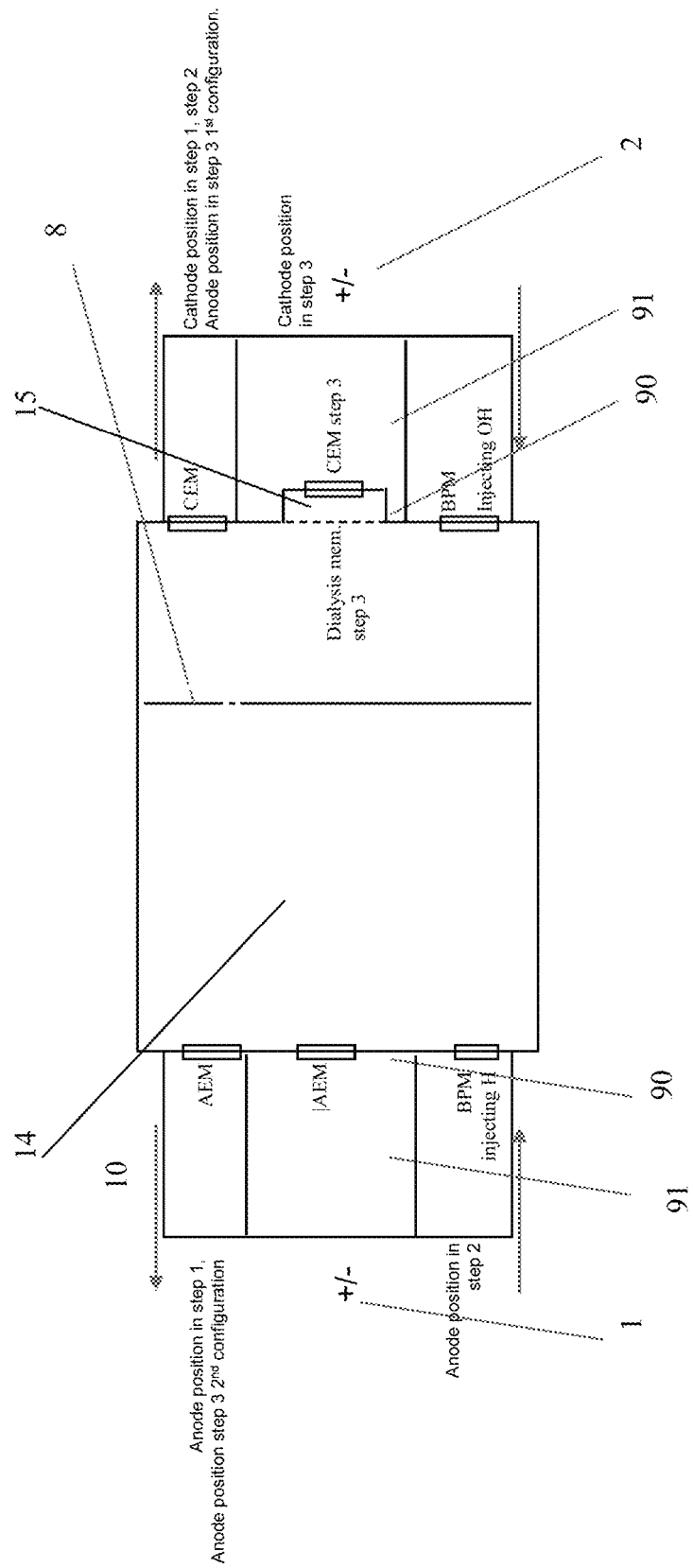

FIG. 9 illustrates an exemplary embodiment of an apparatus as described herein. A voltage applied between two electrodes (1 and 2) can move charged molecules towards the appropriate electrode (cathode or anode, depending on charge). The charged molecules can be moved, for example from the first sub-chamber (14) through the dividing membrane (8) into the second sub-chamber (15) (or in the opposite direction as desired, depending on the configuration of electrodes). The pH of each sub-chamber can be regulated and changed using the ion injectors/extractors. In this case, 92, 93, 94, 95, 96, 97, and 98 are selective membranes and are part of the on injectors/extractors. In one embodiment, 92 and 94 are anion exchange membranes, 93, 96, 97, and 98 are anion exchange membranes and 95 is a bipolar membrane. In this configuration and, initially current is released through membranes 92 and 96, changing the ionic strength, followed by a release of current through membranes 95 and 98, changing the pH. Subsequently, current alternatively passed through membranes 93 and 97, and through 94 and 97, to move charged molecules between 14 and 15. Other configurations are possible as described herein depending on whether ionic strength or pH is to be increased or decreased, and in which direction a particular charged molecule is to be moved. Optionally, the first sub-chamber (14) can include one or more outlet (10) and inlet (9). Similarly, the second sub-chamber (15) can include one or more outlet (11) and inlet (12).

Figure 10:
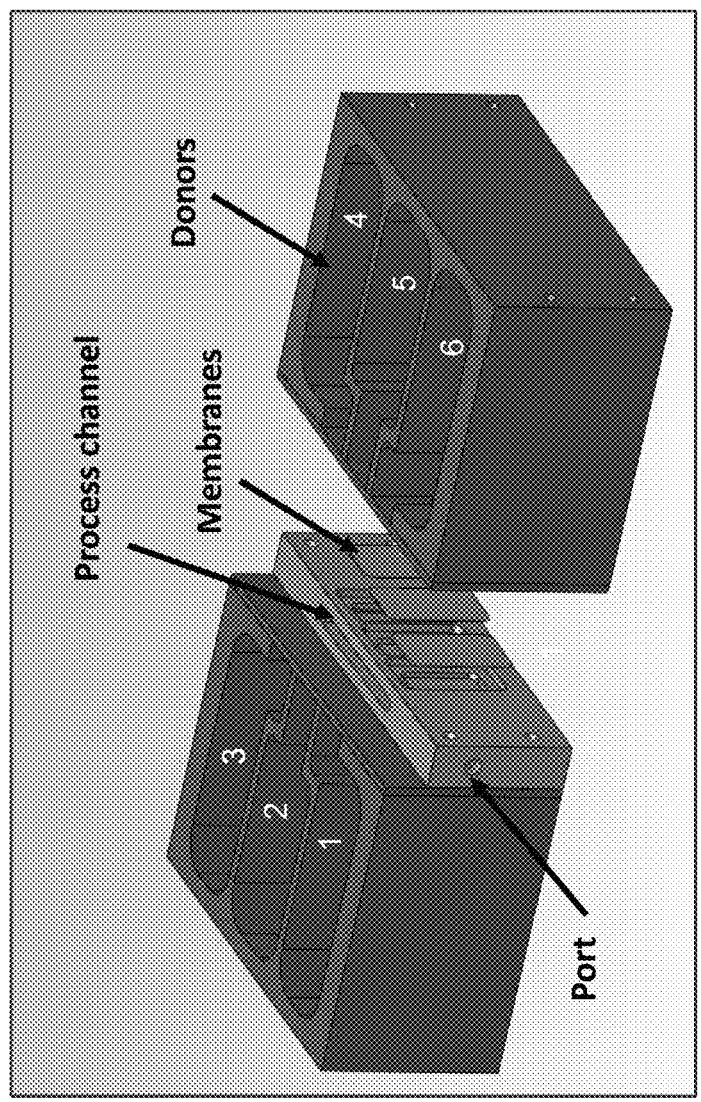

FIG. 10 is a schematic drawing of an apparatus as described in the Example.

Figure 11:
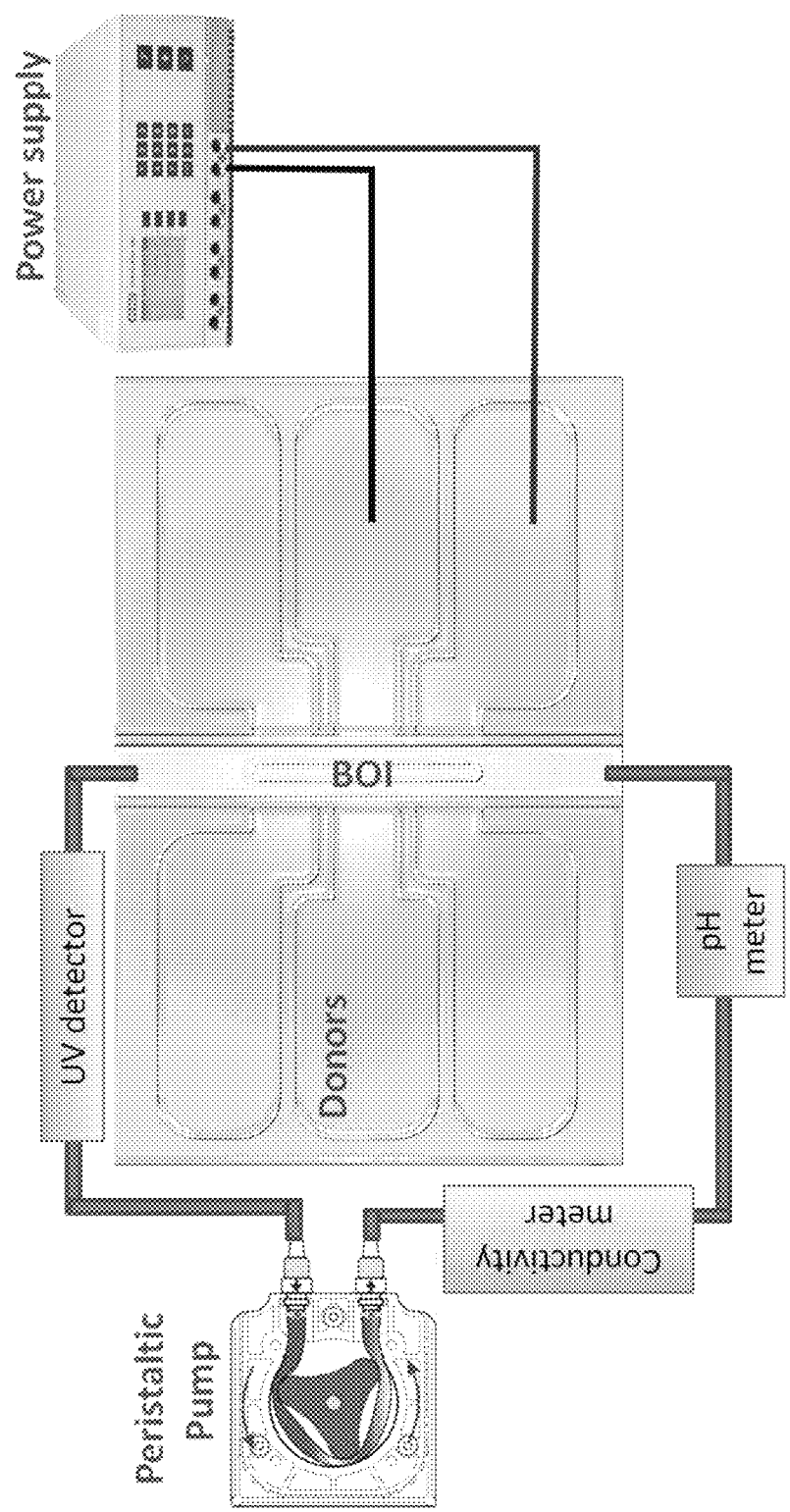

FIG. 11 is a schematic drawing of a system as described in the Example.

Figure 12:
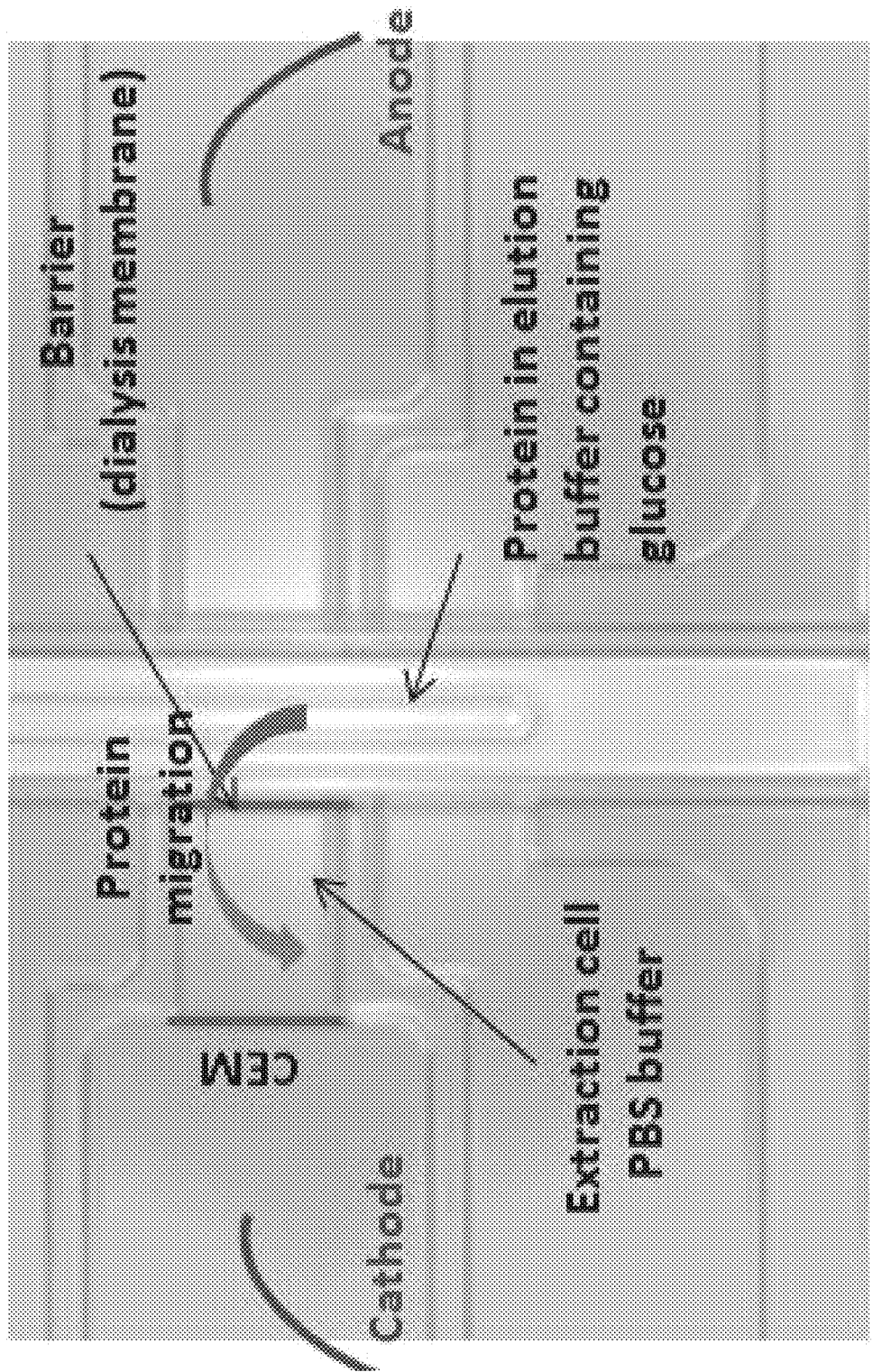

FIG. 12 illustrates an apparatus for moving charged molecules through membranes as described in the Example.

DETAILED DESCRIPTION OF THE INVENTION

I. Introduction

An apparatus is provided that allows for fractionation of samples by pH-dependent charge, thereby allowing for purification of sample components. The apparatus provides a chamber divided into at least two sub-chambers by a membrane (referred to as a "dividing membrane") that substantially blocks flow of fluid between the sub-chambers but allows for movement of some or all of the sample components (e.g., proteins, nucleic acids, etc.) across the membrane in the presence of an electrical current. The two sub-chambers each are in electrical communication with an electrode such that a voltage can be applied between the electrodes and therefore across the two sub-chambers.

One or more of the sub-chamber can be loaded with the sample and the pH of the sub-chambers is adjusted such that some components in the sample are charged. For example, the overall charge of a component will depend on the pI of that component. If the pH is higher than the pI, the component will have an overall negative charge and if the pH is lower than the pI, the component will have an overall positive charge. Upon application of a voltage across the electrodes, positively-charged components will move towards the negative electrode (cathode) and the negatively-charged components will move towards the positive electrode (anode). If one knows the pI of a target molecule in the sample, the pH and electrodes can be designed, as detailed herein, to purify the target molecule from other components of the sample.

An advantage of embodiments described herein is the inclusion of an ion "injector/extractor" (discussed further below) that allows for changing of the pH of a solution in the apparatus without changing of buffers, etc. This allows for changing the pH one or more times during a purification, thereby allowing selection of components using more than one pH "cut-off," or in embodiments in which active enzymes are employed, matching pH conditions to the enzymes. The different charge of different components allows for separation of components by charge by an electric field. Thus, by employing pH changes during the process, charge of various components can be changed, thereby allowing multiple rounds of separation. For example, one can set the pH slightly above the pI of a target (such that the target is negatively charged) and separate all positively-charged molecules from the target. Subsequently, the pH can be changed to slightly below the pI of the target (making the target positive) and all negatively-charged components can be removed, thereby separating all components from the target except for any components with a very similar pI to the target.

The methods can be adapted for various purposes. For example, the methods can be adapted to selected peptides of a particular size by using a membrane having a particular molecule weight size restriction or to select molecules of a certain pI from molecules having a higher and/or lower pI.

II. Apparatus

A basic design of an embodiment of an apparatus of the invention is illustrated as in FIG. 1. Two sub-chambers (14 and 15) together form a chamber, which is divided by a membrane (8). For ease of communication, the left sub-chamber is referred to as a "first" sub-chamber and the right sub-chamber is referred to as a "second" sub-chamber, however the orientation of the two sub-chambers can be reversed if desired. Generally, as used herein, the second sub-chamber is the sub-chamber into which the components are ultimately moved and from which target molecules are collected and/or waste molecules removed. The apparatus can be designed to receive a sample in the first sub-chamber or in both the first and second sub-chambers when the second sub-chamber is used for collection. Accordingly, in some embodiments, the entire chamber can be open from the top or, for example, can have a removable or hinged lid. Thus, in some embodiments, a sample can be loaded from the top as desired. Alternatively, or in combination, the first and/or second sub-chambers can have one or more inlet for introduction of a sample. In some embodiments, the first and/or second sub-chamber can have one or more outlet for removing fluids from the second chamber.

The membrane (8) (i.e., the dividing membrane) will substantially or completely block flow of fluids between the sub-chambers, but will allow movement of components of the sample and smaller molecules across the membrane, especially when charged and in the presence of an electrical field. For example, protein and nucleic acid components of a sample can flow across the membrane. Examples of membranes can include, for example, low-binding modified cellulose membranes such as polysulfonate membranes. In some embodiments, the membrane (8) can be covered with a layer of cross-linked polymer (e.g., polyacrylamide, agarose, etc.) to prevent diffusion of components across the membrane in the absence of an electric field. As noted below, in some embodiments, the membrane can have pores of a particular size to exclude molecules larger than a particular size ("cut-off") while allowing for smaller molecules to pass across. For example, in some embodiments, the molecular weight cut-off is about 10, 15, 16, 17, 18, 19, 20, 21, 22, 23, 24, 25 kDa.

A first electrode is in electrical communication with the first sub-chamber and a second electrode is in electrical communication with the second sub-chamber. "In electrical communication" means that the first and second electrodes are capable of generating a voltage across the two sub-chambers (14, 15) and dividing membrane (8). For example, in some embodiments, the first electrode is within, or adjacent to, the first sub-chamber and the second electrode is within, or adjacent to, the second sub-chamber.

In some embodiments, a membrane (different from the membrane (8) that divides the sub-chambers), referred to herein as a "separation membrane" can separate the electrodes from the fluid in the sub-chambers, thereby preventing contact of components of a sample to the electrodes (which might otherwise denature them). In some embodiments, the membranes separating the electrodes from the sub-chambers have a molecular weight cut-off of, for example, about 200, 500, 100, 2000, 3000, 4000, or 5000 Da, thereby allowing small ions to contact the electrodes but not larger components of a sample such as protein or peptides.

The orientation (+/−) of the electrodes will depend on the desired result. FIGS. 1 and 2 show (left side of figure) the cathode (−) adjacent to the first sub-chamber and (right side of figure) the anode (+) adjacent to the second sub-chamber. However, it should be appreciated the orientation could be reversed such that the anode (+) is adjacent to the first sub-chamber and the cathode (+) is adjacent to the second sub-chamber. As discussed below, the orientation will depend in part on the pI of the target and contaminants, and the relative charge of contaminants and target molecules to be purified. The electrodes can be linked to a controller to control voltage, and optionally orientation of current, across the electrodes.

In some embodiments, the sub-chambers will have substantially the same size and/or will hold the same volume of solution. Alternatively, in some embodiments, the first sub-chamber is substantially larger (holds more volume) than the second sub-chamber.

In some embodiments, the apparatus can comprise a conductivity gauge, a pH gauge, or both. The precise position of the gauge(s) can vary as desired. For example, a pH or conductivity gauge can be placed in the first and/or second sub-chambers. Signals from the gauges can be transferred back to a central electronic controller thereby allowing for modification of the compartment(s) current to regulate pH and conductivity as desired. Independent electronic control of the voltage and/or current of each compartment pair can be controlled via an electronic controller, which can comprise a computer, microprocessor, etc.

In some embodiments, a pump can be included to move the solution through the sub-chamber, e.g., from a reservoir through the sub-chamber, passed the compartments, to a destination. The precise position of the pump can vary as desired, and can be located, for example, between a reservoir and the compartments, between compartments, or between the destination and the compartments. In some embodiments fluids are circulated by electro-osmotic pumping.

Each of the two sub-chambers will also comprise a mechanism to control pH of fluid in the sub-chambers. In some embodiments, the mechanism will comprise a proton/anion injector/extractor and a hydroxide/cation injector/extractor (described in more detail below) adjacent to, or in fluid communication with, a sub-chamber.

In some embodiments, the ion injectors/extractors are adjacent (i.e., directly linked) to a sub-chamber thereby directly affecting the pH of the solution in a sub-chamber. Such an embodiment is depicted in FIG. 1, where for example, injector/extractor compartments 4A, 6A, 5A, and 7A are adjacent to first sub-chamber (14) and injector/extractor compartments 4B, 6B, 5B, and 7B are adjacent to second sub-chamber (15).

In other embodiments, the injector/extractor compartments can be placed adjacent to a reservoir and the solution in the reservoir can be in fluid communication (e.g., via tubing) with the solution in a sub-chamber. Such an embodiment is depicted in FIG. 2, where for example, injector/extractor compartments 4A, 6A, 5A, and 7A are adjacent to first reservoir and injector/extractor compartments 4B, 6B, 5B, and 7B are adjacent to second reservoir, wherein the first reservoir is in turn linked by tubing (9, 10) to the first sub-chamber and the second reservoir is linked by tubing (11, 12) to the second sub-chamber. Optionally, one or more pump can be used to move solution from the reservoirs to the sub-chambers (e.g., 13A and 13C in FIG. 2). As shown in FIG. 2, an additional inlet (and optionally an additional pump (13B)) can be used to provide fresh solution from an external source. In some embodiments, the reservoirs and/or sub-chamber(s) can include a stir bar or other mechanism for stirring and mixing the solution in the various areas.

As discussed in more detail below, the ion injectors/extractors have an associated electrode for generation of ion injection or extraction. In some embodiments, the same electrodes in the ion injector/extractor act as the electrode for moving (electrophoresing) charged molecules across the membrane separating the first and second sub-chambers. In some aspects, one or more ion injector/extractor can be used solely to control pH and/or ionic strength while a different ion injector/extractor directs current also through the dividing membrane. In one configuration, one (or one set of) ion injector/extractor(s) control proton and/or hydroxyl concentrations, i.e., pH, optionally a second (or second set of) ion injector/extractor(s) control ionic strength, and yet another (or another set of) ion injector/extractor(s) is configured such that current from the electrode in the injector/extractor control goes through both a selective (e.g., cation exchange, anion exchange, bipolar) membrane and the dividing membrane, with the region between the membranes being a sub-chamber, e.g., to collect purified charged molecules.

An aspect of such embodiments is depicted in FIG. 9. Thus, in some embodiments, initially the pH and/or ionic strength can be set with ion injectors configured as follows:
Step 1: Anode operating an AEM and cathode operating a CEM (reducing salt);
Step 2: Anode operating a BPM injecting protons and cathode operating a CEM (reducing pH);
Step 3: charged molecules transfer. Two configurations (e.g., switched intermittently):
1st configuration (ion insertion): Anode operating a CEM and a cathode operating a CEM & dialysis membrane;
2nd configuration (ion removal): Anode operating an AEM; cathode operating a CEM & dialysis membrane.

It will be appreciated that other configurations are also possible depending on whether the ionic strength is to be increased, decreased, or both at different times.
Injectors/Extractors An ion "injector/extractor" refers to one or more compartments, separated from a sub-chamber or other vessel (e.g., such as a reservoir), by a membrane(s) that is ion selective, in wherein the compartment(s) each contain an electrode. For example, exemplary injector/extractors are depicted as 4A, 4B, 5A, 5B, 6A, 6B, 7A, and 7B in FIGS. 1 and 2. Depending on the specific ion selectivity of the membrane, as well as the orientation of the current (e.g., presence of the anode and cathode) in the various compartments, the compartments can be designed to inject protons, other cations, hydroxide ions, or other anions through the selective membrane and into the adjacent sub-chamber. Or, as explained below, the orientation of the compartments, membranes, and current can also be designed to extract protons, other cations, hydroxide ions, or other anions from the sub-chamber through the selective membrane and into the compartment.

A basic exemplary apparatus configuration comprises a sub-chamber as described herein in fluid communication with at least a first and a second compartment, wherein the first compartment is divided from the sub-chamber by a first selective membrane and the second compartment is divided from the sub-chamber by a second selective membrane. Selective membranes allows for movement of certain ions (e.g., cations or anions or protons and hydroxide ions) while inhibiting transport of other ion types across the membrane. In many embodiments, the first and second selective membranes have different selective properties. Examples of selective membranes include, e.g., anion selective membranes, cation selective membranes, and bipolar selective membranes. The first and second compartments each comprise an electrode (an anode in one compartment and a cathode in the other compartment) to form a circuit via the solution in the compartments and the sub-chamber. Two compartments that form a circuit are referred to herein as a "compartment pair" or a "pair of compartments." In some embodiments, a third or further additional compartment can interact with the pair, for example, where a cathode of one compartment generates current for two or more different anode-containing compartments (or vice versa in which there is one anode and two or more cathodes). Depending on the direction of the current and the type of selective membrane dividing the compartments from the sub-chamber, the solution in the sub-chamber will accumulate protons, hydroxide ions, other anions or cations, or in some configurations will transfer cations and/or anions to the side sub-chambers. By controlling the current and configuration, one can thereby control the pH and/or ionic strength of the solution in the sub-chamber.

Pairs of compartments, each forming a separate circuit through the solution in the sub-chamber and having different configurations of selective membranes, can be combined, to achieve desired results. For example, a first and second compartment can form a circuit and inject chloride anions and protons into the solution while a third and fourth compartment can form a separate circuit and inject hydroxide and sodium cations into the solution in the sub-chamber, thereby raising the ionic strength, and depending on the relative flow of protons and hydroxide ions, altering the pH. As explained below, many other configurations are possible. The use of "first," "second," "third," etc., is used for convenience in labeling and is not intended to impart any other meaning.

The membranes "divide" the compartments from the sub-chamber by forming a barrier that separates solution in a compartment from the sub-chamber, e.g., at least to the level of solution in the sub-chamber. For example, in embodiments in which the sub-chamber is open at the top (or alternatively, has a top cover that can be removed), the membranes can be designed to completely divide a compartment from the sub-chamber at least up to the level of solution in the sub-chamber and/or compartment, or to a level designated as a maximum for solution loading. As desired, the membranes can be designed to be higher than the solution level so as to avoid accidental transfer (e.g., splashing) from one portion to another. If desired, the membranes can be "framed" by a solid material (e.g., plastic) or otherwise anchored between the sub-chamber and the compartment. The ion specific membranes can be further supplemented with neutral membranes such as dialysis membranes to prevent, e.g., contact of molecules in the solution with the ion specific or bipolar membranes.

The electrodes can be formed from any conducting or semi-conducting substance. For example, in some embodiments, one or more electrode comprises a metal. In some embodiments, the metal is zinc, copper, or platinum.

A. Ion injectors

A number of different ion injectors can be designed. International Patent Application Publication No. WO2009/027970 describes methods and devices (referred to herein as "proton/hydroxide injectors") useful in producing local concentrations of protons or hydroxide ions, proton or hydroxide concentration gradients, and desired proton or hydroxide concentration topographies in an environment, such as an electrolyte solution, a gel, and the like. International Patent Application Publication No. WO2011/021195 and WO2011/

021196 describe methods and devices for isoelectric focusing proton/hydroxide injectors and also describes display of data.

Proton/hydroxide injector technology can be used to affect the pH of the solution in a sub-chamber. Briefly, in some embodiments, the proton/hydroxide injector comprises a compartment adjacent to a sub-chamber, with an electrode inside the compartment, and a bipolar membrane separating the compartment from the channel. See, e.g., FIGS. 3-4. A bipolar membrane is an ion-exchange membrane having a structure in which a cation-exchange membrane and an anion-exchange membrane are joined together, and allows for water molecules to be split into protons and hydroxide ions. Voltage applied between the compartment and the channel divided by the bipolar membrane leads to water splitting and injection of protons or hydroxide ions into the channel. Some advantages of this technology can include, for example, bubble-free water hydrolysis and injection of generated ions directly to the channel, allowing short response time (e.g., if desired, below 1 minute).

By applying the appropriate voltage to the anode and cathode, and therefore a current across the solution in the compartments and sub-chamber, charged molecules will move accordingly. In some embodiments, the charged molecules can be added to the anode or cathode compartment, and subsequently the voltage is applied, thereby delivering the charged molecule to the sub-chamber at a time determined by the user.

The direction of movement of the molecule will depend on the charge of the molecule and the polarity of the applied voltage.

Injection of a non-proton, non-hydroxide ion from a compartment into the sub-chamber can be achieved, for example, by pairing a first compartment comprising a cathode in the compartment and an anion selective membrane dividing the first compartment and the sub-chamber with a second compartment having an anode. In this configuration, the first compartment will inject anions present in the first compartment solution in the presence of a current between the cathode and the anode and thus is referred to as an "anion injector." For example, if the compartment solution comprises chloride anions, the chloride anions will be transferred across the anion selective membrane into the sub-chamber in the presence of a current between the cathode and the anode. An embodiment of this aspect is depicted in FIG. 5, in which the top compartment in the Figure injects chloride ions in the presence of a current through the top and bottom chamber ("top" and "bottom" as used with reference to figures, refer to the top and bottom of the figure, and not necessarily the top and bottom of the apparatus). It should be appreciated that this configuration is not limited to injection of chloride ions. Any anion present and capable of passing through the anion selective membrane can be transferred from the compartment into the sub-chamber. FIG. 5 further depicts an aspect in which the first compartment is paired in a circuit with a second compartment, the second compartment divided from the sub-chamber by a bipolar membrane. In this aspect, the second chamber injects protons into the sub-chamber and thus is referred to as a "proton injector."

As shown in FIG. 5, application of a voltage between the anode and cathode leads to water splitting by the bipolar membrane (bottom compartment). Protons are injected into the sub-chamber and titrate the solution flowing in the sub-chamber to the desired reduced pH. Hydroxide ions generated in the splitting process recombine with protons generated by water hydrolysis in the anode. Because the current is the same across the bottom compartment, the pH in the anode compartment is maintained (in the absence of further electrochemistry) in its initial value. Due to charge neutrality and the anion selective membrane separating the cathode (top as depicted) compartment from the sub-chamber, anions (e.g., chloride ions) are injected from the cathode (top) compartment into the sub-chamber. Thus, the solution in the sub-chamber as depicted in FIG. 5 is titrated with HCl, thereby lowering the pH. This aspect is also depicted in FIGS. 1 and 2, compartments 4A-B and 5A-B, if 4A-B each comprise a cathode and an anion-selective membrane and 5A-B each comprise an anode and a bipolar membrane.

However, it is also possible for a chamber having an anion selective membrane to inject hydroxide ions into the sub-chamber. This can be achieved, for example, by raising the concentration of hydroxide ions (i.e., raising the pH) in the chamber, thereby allowing for a higher concentration of hydroxide ions to be available to move into the sub-chamber when the current is applied (when the solution in the chamber is neutral, the concentration of hydroxide ions is negligible). An embodiment of this option would be a configuration as shown in FIG. 5, but with the solution in the top chamber being basic.

Alternatively, injection of a non-proton, non-hydroxide ion from a compartment into the sub-chamber can be achieved, for example, by pairing a first compartment comprising an anode in the compartment and a cation selective membrane dividing the first compartment and the sub-chamber with a second compartment. In this configuration, the first compartment will inject cations present in the first compartment solution into the sub-chamber in the presence of a current between the cathode and the anode and thus is referred to as a "cation injector." For example, if the compartment solution comprises sodium cations, the sodium cations will be transferred across the cation selective membrane into the sub-chamber. An embodiment of this aspect is depicted in FIG. 6, in which the top compartment in the Figure injects sodium ions in the presence of a current through the top and bottom chamber. However, it should be appreciated that this configuration is not limited to injection of sodium ions. Any cation present and capable of passing through the cation selective membrane can be transferred from the compartment into the sub-chamber. FIG. 6 further depicts an aspect in which the first compartment is paired in a circuit with a second compartment, the second compartment divided from the sub-chamber by a bipolar membrane. In this aspect, the second chamber injects hydroxide ions into the sub-chamber and thus is referred to as a "hydroxide ion injector." This aspect is also depicted in FIGS. 1 and 2, compartments 6A-B and 7A-B, if 6A-B each comprise an anode and a bipolar membrane and 7A-B each comprise a cathode and a cation-selective membrane.

In contrast to the aspect depicted in FIG. 5, in FIG. 6 hydroxide ions are injected into the sub-chamber and titrate the solution flowing in the sub-chamber to the desired increased pH. Protons generated in the splitting process recombine with hydroxide ions generated by water hydrolysis in the cathode. Because the current is the same across the bottom compartment the pH in the cathode compartment is maintained in its initial value in the absence of other electrochemical processes. Due to charge neutrality and the cation selective membrane separating the anode (top as depicted) compartment from the sub-chamber, cations (e.g., sodium ions) are injected from the anode (top) compartment into the sub-chamber. Thus, the solution in the sub-chamber as depicted in FIG. 6 is titrated with NaOH.

However, it is also possible for a chamber having a cation selective membrane to inject hydrogen ions into the sub-chamber. This can be achieved, for example, by raising the concentration of hydrogen ions (i.e., lowering the pH) in the chamber, thereby allowing for a higher concentration of hydrogen ions to be available to move into the sub-chamber when the current is applied (when the solution in the chamber is neutral, the concentration of hydrogen ions is negligible). An embodiment of this option would be a configuration as shown in FIG. 6, but with the solution in the top chamber being acidic.

Any number of compartment circuit pairs can be combined depending on the goal to be achieved. In these embodiments, electrodes in different pairs of compartments can be controlled independently so that different voltage or current can be applied to different pairs, as desired.

B. Ion Extractors

Also provided are combinations of compartments that transfer ions from the solution in the sub-chamber into the compartments (i.e., acting as ion extractors).

In some aspects, a pair of compartments extract a non-proton, non-hydroxide ion from the sub-chamber into a compartment while adding a proton or hydroxide ion into the sub-chamber from a different compartment. This can be achieved, for example, by pairing a first compartment comprising a cathode in the compartment and a cation selective membrane dividing the first compartment and the sub-chamber with a second compartment having an anode. In this configuration, the first compartment will extract cations present in the sub-chamber and transfer the cations into the first compartment and thus is referred to as a "cation extractor." For example, if the sub-chamber solution comprises sodium ions, the sodium ions will be transferred across the cation selective membrane from the sub-chamber in the presence of a current between the cathode and the anode. An embodiment of this aspect is depicted in FIG. 7, in which the top compartment in the Figure extracts cations (sodium ions depicted) from the sub-chamber in the presence of a current through the top and bottom chamber. However, it should be appreciated that this configuration is not limited to extraction of sodium ions. Any cation present and capable of passing through the cation selective membrane can be transferred from the sub-chamber into the compartment. FIG. 7 further depicts an aspect in which the first compartment is paired in a circuit with a second compartment, the second compartment divided from the sub-chamber by a bipolar membrane. In this aspect, the second chamber injects protons into the sub-chamber while the first chamber extracts sodium cations.

Alternatively, extraction of a non-proton, non-hydroxide ion from the sub-chamber into a compartment while adding a proton or hydroxide ion into the sub-chamber from a different compartment can be achieved, for example, by pairing a first compartment comprising an anode in the compartment and an anion selective membrane dividing the first compartment and the sub-chamber with a second compartment. In this configuration, the first compartment will extract anions present in the sub-chamber and transfer the anions into the first compartment and thus is referred to as an "anion extractor." For example, if the sub-chamber solution comprises chloride ions, the chloride ions will be transferred across the anion selective membrane out of the sub-chamber in the presence of a current between the cathode and the anode. An embodiment of this aspect is depicted in FIG. 8, in which the top compartment in the Figure extracts anions (chloride ions depicted) from the sub-chamber in the presence of a current through the top and bottom chamber. However, it should be appreciated that this configuration is not limited to extraction of chloride ions. Any anion present and capable of passing through the anion selective membrane can be transferred from the sub-chamber into the compartment. FIG. 8 further depicts an aspect in which the first compartment is paired in a circuit with a second compartment, the second compartment divided from the sub-chamber by a bipolar membrane. In this aspect, the second chamber injects hydroxide ions into the sub-chamber.

III. Methods

The apparatuses described herein can be used to purify one or more target molecule from complex (e.g., biological or other) samples. The methods take advantage of different charges of components of a sample to separate components having a particular charge from neutral components and/or components that have the opposite charge. The charge of components can be controlled because charge of components is a function of the pH of the solution. Therefore by controlling the pH, the charge of a component can be controlled. For example, the pI of a component is the pH at which charge of the component is neutral. If the pH of the solution is lower than the pI, then the charge the component is positive. If the pH of the solution is higher than the pI, then the charge the component is negative. Different components of a sample will generally having different pIs thereby allowing for conditions in which different components have different charge. For instance, if molecule A has $pI_A$ and molecule B has $pI_B$, and $pI_A < pI_B$, and the pH of the solution is between $pI_A$ and $PI_B$, then molecule A will have an overall positive charge and molecule B will have an overall negative charge. By applying a voltage to the electrodes (e.g., labeled 1 and 2 in FIGS. 1 and 2) across the membrane dividing the two sub-chambers, positively-charged components will move towards the cathode and negatively charged components will move towards the anode. Because the membrane dividing the sub-chambers generally blocks flow of fluid between the sub-chambers, but allows movement of the sample components, application of the voltage will enrich the sub-chambers for differently charged fractions.

As an example, a sample is filled only in the first sub-chamber (14, FIG. 1) and a buffer fills the second sub-chamber, the pH of the solutions in the two sub-chambers is adjusted using the injector/extractors such that some components in the solution are negatively charged and then the voltage between the electrodes (1 and 2) is applied, moving negatively-charged components to the second sub-chamber (15). If the components moved to the second sub-chamber are desired (i.e., are target molecules), they can be collected, and optionally further purified, etc. Alternatively, if the negatively-charged components are not target molecules, the contents of the second sub-chamber can be moved to waste. Of course, the same method can be applied in reverse, that is, the pH can be controlled to generate positively-charged components that are moved into a second sub-chamber comprising a cathode and collected or moved to waste as desired. It should also be appreciated that while the example above involved loading of the sample into the first sub-chamber only, in some embodiments, the sample can be loaded into both sub-chambers.

One advantage of the inclusion of pH injector/extractors is that the pH of the solution in the sub-chambers can be changed and multiple rounds of purification can occur. For example if a target protein with a specific pI is to be captured, the pH of the chambers is adjusted to pH slightly (for example 0.5 pH units) below the pI of the target protein. An electric field is applied such that the first sub-chamber electrode is negative (cathode) and the second sub-chamber electrode is positive (anode). Proteins with a pI below the pH will migrate into the second sub-chamber and can be collected or disposed to waste, e.g., by providing flow with a pump. Subsequently, in some embodiments, the pH in the chambers is adjusted to pH slightly above the pH of the protein of interest (for example 0.5 pH units above) the pI of target protein. This will cause the protein of interest to migrate into the second sub-chamber and can be collected in more pure and concentrated form than in the original sample. The proteins in the second sub-chamber can be eluted in the end of the separation or continuously while the separation is being performed. Continuous elution may provide additional dimension of separation based on the mobility of the proteins (charge to size).

The described methodology can also be used for fractionation of proteins, peptides, or other sample components (in an apparatus having a negatively-charged electrode in the first sub-chamber and a positively-charged electrode in the second sub-chamber) by adjusting the pH from low to high and moving fractions with pI below the pH to the second sub-chamber chamber, then adjusting the pH higher and moving the next fraction to the second sub-chamber. By this method, multiple fractions can be captured.

Fractionation can also be performed by starting with high pH and decreasing the pH stepwise and collecting the fractions in the right chamber by applying electric field in an apparatus having a positively-charged electrode in the first sub-chamber and a negatively-charged electrode in the second (collection) sub-chamber.

Alternatively continuous separation may be achieved by continuously changing the pH of the chambers and continuously removing the proteins/peptides from the second sub-chamber. In this way, continuous separation based on pI can be achieved.

In some embodiments, chemical or enzymatic reactions can be performed in one or more sub-chamber. For instance, in some embodiments, the apparatus can be used to set the optimal pH for a particular enzyme or reaction, or can be changed to accommodate a second reaction or enzyme after the first reaction is no longer desired.

In some embodiments, the optimal size of a product can be selected. For instance, the membrane separating the two sub-chambers can be selected to have a size cut-off, i.e., such that larger molecules are blocked and smaller molecules can pass through the membrane. As one example, some mass spectrometers are capable of fragmenting larger molecules and are most effective in the 20 kDa range. The methods described herein can be adapted to enrich for peptides of about 20 kDa by selecting a membrane having a 20 kDa cut-off, thereby avoiding significant amounts of peptides substantially larger or smaller than the target size.

In some embodiments, a sample comprising proteins and/or peptides and in contact with one or more proteolytic enzyme(s) is placed in the first sub-chamber, wherein the membrane dividing the sub-chambers is size-selective. The peptides, once cleaved to the cut-off size, can be moved by the electric field to the second sub-chamber (which does not contain the enzyme), thereby allowing for enrichment of the peptides at a certain size. In some embodiments, the optimal pH of an enzyme is selected for the first sub-chamber for a period of time and then the pH is changed to set the desired charge of the target molecules and then the target molecules can be moved to the second sub-chamber by the electric field and collected. If desired, different enzymes can be added, for which the optimal pH can be set for each enzyme in series, optionally moving peptides of appropriate size between the optimal pH changes, thereby moving those peptides sufficiently small to pass through the membrane before the subsequent enzyme is used on the remaining, larger, proteins. As noted above, this process, for example, allows researchers to shift the average peptide size of an enzyme-treated sample to a larger size (up to 20 kDa for example), thereby increasing the effectiveness of the mass spectrometry instruments capable of analyzing larger fragments, and increasing the coverage of protein sequences measured by mass spectrometry.

Examples

This example provides a system that facilitates digital adjustment of any type of charged molecule (ions). In this technology, protons and hydroxyl ions can be injected using proton and hydroxyl injectors having bipolar membranes. Salts can be introduced and removed using ion exchange membranes. The ability to electrically generate and modify salt profiles of protein solutions opens new ways to control biological processes and to replace existing traditional instrumentation. The following description demonstrates how salt conditioning technology is utilized to a certain application. It should be understood, however, that this description does not limit the technology from other possible applications.

The main application described here, aims to replace an existing method to handle proteins coming out of chromatography columns. Such proteins come out in elution buffers, which generally are not compatible for later procedures (such as activity tests, crystallography, or additional purification steps). These buffers should therefore be replaced before any additional manipulation is performed on the protein. Traditionally, this buffer adjustment is achieved either by dialysis or by centrifugation. The main disadvantage of the first method is the long time it takes to complete the buffer exchange. The main disadvantage of the second method is material loss. In addition, both methods suffer from the fact that they are performed "off line", that is, they are not linked to the operation of the chromatography instrument. Instead, the user has to take the elution buffer coming out of the chromatography system and introduce it to either a dialysis or a centrifugation apparatus. The system described here is able to reduce substantially the time needed for buffer exchange and has relatively low material loss. Also, the fact that the system operates electrically, makes it very easy to link it to chromatography systems. In such integrated "chromatography-conditioning system", proteins could go through several columns (conditioned every time they enter the next column) and come out purified in any desired buffer.

Description of the System

The operating unit in the system comprises a 5 ml process chamber and six auxiliary reservoirs connected to the chamber via two cation exchange membranes (CEM), two anion exchange membranes (AEM), and two bipolar membranes of opposite polarity, (BPM-H polarity which injects protons, and BPM-OH polarity which injects hydroxyl ions), detailed in table 1 and FIG. 10.

TABLE 1

| Reservoir | Membrane |
| --- | --- |
| 1 | BPM H |
| 2 | CEM |
| 3 | CEM |
| 4 | AEM |
| 5 | AEM |
| 6 | BPM OH |

This unit is connected to the rest of the components according to FIG. 11. A power supply connects two operating auxiliary reservoirs and drives current from one to the other through the process chamber. In order to enhance solution mixing and remove heat generated by the electric current, the solution is circulated in and out of the chamber. This is achieved using a peristaltic pump that connects to the chambers' ports through Tygon pipes. Along this circular path, a UV detector, a conductivity meter, and a pH meter are connected to monitor protein absorbance, salt concentration and pH levels, respectively. Optionally, the mixing inside the chamber is further enhanced by placing three magnetic bars in the process chamber and placing the latter on a magnetic plate.

pH and salt were controlled by wiring the appropriate auxiliary reservoirs and filling them with the appropriate solution. For example, in order to insert H+ ions, reservoirs 1 and 2 (see FIG. 10) were filled with 0.1M $Na_2SO_4$. The anode was then placed inside reservoir 1, the cathode in reservoir 2, and a current of, for example, 50 mA was applied. This setup injected protons inside the chamber from the BPM-H and removes cations out through the CEM to reservoir 2. Alternatively, the cathode can be wired to reservoir 4 containing 0.1M $Na_2SO_4$. In this case, anions ($SO_4^{-2}$) will enter the chamber through the AEM of reservoir 4.

When inserting buffers, one fills the appropriate auxiliary reservoir with a solution containing excess amount of buffer ions, and applies an electric current appropriate to their charge. Also, since the electrical charge of buffer ions is pH dependent, one sets the pH in the buffer solution to a level in which these molecules have the desired charge. If, for example, Tris is to be inserted, then a 0.5 M of such buffer is prepared at pH 7. Since Tris has a pKa of 8, setting the pH to 7 will ensure that most of the Tris molecules are in their positively charged state. Then, the buffer is inserted to either reservoir 2 or 3 with contact to the anode. The cathode is placed in a $Na_2SO_4$ solution inside, for example, reservoir 4. In this case, upon current application, Tris will enter the chamber from the anode side, and $SO_4^{-2}$ will enter through the cathode side. Optionally, ice is inserted to the reservoirs to improve heat removal from the chamber.

Table 2 depicts various possible wirings and their corresponding ions flows.

| Cathode | Anode | | |
|---|---|---|---|
| | AEM (res. 2, 3) | CEM (res. 5, 6) | BPM-H (res. 1) |
| AEM (res. 2, 3) | Anions out Anions in | Cations in Anions in | Protons in Anions in |
| CEM (res. 5, 6) | Anions out Cations out | Cations in Cations out | Protons in Cations out |
| BPM-OH (res. 4) | Anions out hydroxyl in | Cations in hydroxyl in | Protons in hydroxyl in |

The operation of the system is as follows.
1) The solution to be conditioned is inserted to the chamber, and appropriate buffers are inserted into the reservoirs.
2) Solution is circulated and mixed by operating the peristaltic pump and magnetic stirring bars.
3) Wiring is set by applying the anode and cathode to the selected reservoirs. The desired current is set in the power supply.
4) Current is applied for a certain time-lapse. Typically 50-100 mA is applied for 30-60 minutes. During this stage, readings from the pH and conductivity meters, as well as the UV detectors can be taken every few minutes to monitor pH level, salt concentration, and protein absorbance, respectively.
5) When salt conditioning is completed, the current is turned off, and the solution is ejected from the system.

Note: As discussed below, some salt conditioning procedures involve applying multiple currents through different reservoirs. This can be done sequentially, that is, repeating steps 3,4 twice or more, each time for a different reservoir pair. Alternatively, this could be done simultaneously by adding more current suppliers and wiring them each to a different reservoir pair.

Data

The ability to insert and extract ions was demonstrated on many types of salt and buffers, summarized in Table 3:

| Salt ions | Buffer |
|---|---|
| phosphate | Phosphate |
| Cl- | HEPES |
| SO4-2 | Tris |
| SDS | MOPS |
| TFA | Carbonate |
| | Imidazole |
| | citrate |

Using these capabilities, salt conditioning of a few elution buffers was demonstrated. The target solution conditioned with the system were standard ones, used for protein storage. These methods were performed with different kinds of proteins whose concentration and activity were tested before and after each procedure to check their recovery. All solutions were 5 ml in volume.

Conditioning H is Tag Elution Buffer:
  Original solution:
  20 mM Tris buffer
  500 mM NaCl
  500 mM Imidazole
  pH 9.5
  Target solution:
  50 mM Tris buffer
  Conditioning Steps:
  Step 1—lowering pH level to 6 (this step is performed to charge the imidazole molecules)
    Anode position: BPM-H (res. 1) in $Na_2SO_4$ 0.1M
    Cathode position: CEM (res. 2/3) in $Na_2SO_4$ 0.1M
    Current & Duration: 100 mA for 40 minutes.
  Step 2—salt removal to 50 mM
    Anode position: AEM (res. 5/6) in $Na_2SO_4$ 0.1M
    Cathode position: CEM (res. 2/3) in $Na_2SO_4$ 0.1M
    Current & Duration: 100 mA for 40 minutes.
  Step 3—Tris insertion
    Anode position: AEM (res. 5/6) in Tris 0.5M pH 7
    Cathode position: CEM (res. 2/3) in $Na_2SO_4$ 0.1M
    Current & Duration: 50 mA for 40 minutes.
Protein Recoveries:
Cytochrome C—
  Original concentration 1 mg/ml
  Protein recovery: 80%-85%, according to absorption measurements at 280 nm
Lipase—
  Original concentration 1 mg/ml
  Protein recovery: 100%, according to absorption measurements at 280 nm
  Protein residual activity: >100%
Anti Rabbit igG—
  Original concentration 0.07 mg/ml
  Protein recovery: 85%, according to absorption measurements at 280 nm
  Protein residual activity: 88%, according to ELISA tests Conditioning Solutions with Neutral Species In addition to the system's capacities discussed above, which all involve removal and insertion of charged molecules, a further improvement was made to condition protein solution containing uncharged molecules. We exploited the fact that proteins are charged molecules to separate them from neutral species by electrically driving them through a barrier (dialysis membrane), leaving behind all uncharged molecules. As shown in FIG. 12, a new CEM membrane placed in the cathode's reservoir defines a new volume ("extraction cell") to which the protein will be extracted. Facing this membrane, a dialysis membrane with 300 kD cutoff (SPECTRUM LABS, cat number 131450), is inserted as one of the membranes of the process chamber. In order to separate neutral molecules from proteins, current was applied across the process chamber causing proteins to move through the dialysis membrane and settle in the extraction cell, while the uncharged molecules stayed behind.

We demonstrated the concept by extracting cytochrome C from an elution buffer of Lentil Lectin sepharose column containing 500 mM of the neutral molecule D-glucose. This column is used for purification of glycoproteins.

Conditioning Lentil Lectin Sepharose Column Elution Buffer:
Original solution:
20 mM Tris buffer
500 mM NaCl
500 mM Glucose
pH 9.4
Solution in Extraction Cell: PBS Buffer
Conditioning Steps:
Step 1—salt removal to 50 mM (performed to enhance protein migration in step 3)
Anode position: AEM (res. 4/5) in $Na_2SO_4$ 0.1M
Cathode position: CEM (res. 2/3) in $Na_2SO_4$ 0.1M
Current & Duration: 100 mA for 40 minutes.
Step 1—lowering the pH level to 3 (performed to create positive charged protein)
Anode position: BPM-H (res. 1) in $Na_2SO_4$ 0.1M
Cathode position: CEM (res. 2/3) in $Na_2SO_4$ 0.1M
Current & Duration: 100 mA for 3 minutes.
Step 3—protein migration to extraction cell. In this step we used two alternative wirings to maintain constant salt concentration inside the chamber. Wiring was switched every few minutes.
$1^{st}$ configuration (ion insertion)
Anode position: CEM (res. 2/3) in $Na_2SO_4$ 0.1 M pH 7
Cathode position: dialysis membrane (res. 2) in PBS
Current & Duration: 50 mA for 3 minutes.
$2^{nd}$ configuration (ion removal)
Anode position: AEM (res. 5/6) in $Na_2SO_4$ 0.1M pH 7
Cathode position: dialysis membrane (res. 2) in PBS
Current & Duration: 150 mA for 15 minutes
Recoveries:
Cytochrome C—
Original concentration 1 mg/ml
Protein recovery:
64% of the original amount inside the extraction cell.
19% of the original amount was left in the chamber
17% was lost.
Glucose—
Extraction cell: 10%
Chamber: 90%

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

What is claimed is:

1. An apparatus, comprising
a chamber divided into a first sub-chamber and a second sub-chamber by a dividing membrane, wherein the dividing membrane blocks or substantially blocks flow of fluid between the first and second sub-chamber; and wherein
the first sub-chamber is in electrical and fluid communication with a first ion injector extractor comprising a first electrode;
the second sub-chamber is in electrical and fluid communication with a second ion injector extractor comprising a second electrode;
and
the second sub-chamber comprises an outlet,
wherein the ion injector/extractors each comprise:
  a. a compartment in fluid communication with a sub-chamber and divided from the sub-chamber by an anion selective membrane, wherein the anion selective membrane is permeable to small anions but not larger molecules; and/or
  b. a compartment in fluid communication with the sub-chamber and divided from the sub-chamber by a bipolar membrane, wherein the bipolar membrane is permeable to small ions but not larger molecules; and/or
  c. compartment in fluid communication with a sub-chamber and divided from the sub-chamber by a cation selective membrane, wherein the cation selective membrane is permeable to small cations but not larger molecules.

2. The apparatus of claim 1, wherein the second sub-chamber is smaller than the first sub-chamber.

3. The apparatus of claim 1, wherein the first electrode is an anode and the second electrode is a cathode.

4. The apparatus of claim 1, wherein the first electrode is a cathode and the second electrode is an anode.

5. The apparatus of claim 1, wherein the injector/extractors are directly linked to the respective sub-chambers.

6. The apparatus of claim 1, wherein the injector/extractors are linked to the respective sub-chambers via tubing or a channel.

7. The apparatus of claim 1, wherein the second sub-chamber further comprises one or more inlet.

8. The apparatus of claim 1, wherein the dividing membrane comprises a layer of cross-linked polymer, thereby inhibiting fluid diffusion.

9. The apparatus of claim 1, wherein the dividing membrane contains pores that allow passage of peptides smaller than a molecular cut-off but substantially block passage of peptides larger than the molecular cut-off.

10. The apparatus of claim 9, wherein the molecular cut-off is about 20 kDa.

11. A method of purifying a target protein(s) or peptide(s) from a sample, the method comprising
providing the apparatus of claim 1;
loading the sample into the first sub-chamber, or the first and second sub-chambers, wherein the first and second sub-chambers contain fluid following the loading,
controlling the injector/extractors to adjust the pH of the fluid in the chamber to a pH such that some components of the sample are charged due to the pH adjustment and some components are not charged;

applying a voltage between the first and second electrode, thereby moving at least some charged components into the second sub-chamber; and removing the fluid in the second chamber including the charged components via the outlet in the second sub-chamber, thereby separating the target protein(s) or peptide(s) in the sample from at least some other components of the sample.

12. The method of claim 11, wherein one or more target protein or peptide is a charged component moved to the second sub-chamber, and the target protein or peptide is collected after the removing.

13. The method of claim 11, wherein the charged components moved to the second sub-chamber are contaminants and discarding the contaminants.

14. The method of claim 11, wherein the sample is loaded into the first sub-chamber only.

15. The method of claim 11, wherein the sample is loaded into the first and second sub-chambers.

16. The method of claim 11, wherein the first electrode is a cathode (negative charge) and the second electrode is an anode (positive charge), and the controlling comprises adjusting the pH of the fluid below the pI of the target protein(s) or peptide(s) such that the target protein(s) or peptide(s) have an overall positive charge and at least some other components of the sample are negatively-charged; and the applying results in movement of the negatively-charged components to the second sub-chamber and the target protein(s) or peptide(s) remain in the first sub-chamber; and removing fluid comprising the moved components from the second sub-chamber and optionally replacing the removed fluid with new fluid in the second sub-chamber; and subsequently controlling the injector/extractors to adjust the pH of the fluid in the chamber to a pH above the pI of the target protein(s) or peptide(s) such that the target protein(s) or peptide(s) have an overall negative charge;

applying a voltage between the first and second electrode, thereby moving the negatively-charged target protein(s) or peptide(s) into the second sub-chamber; and removing and collecting the fluid in the second chamber, including the target protein(s) or peptide(s), via the outlet in the second sub-chamber, thereby separating the target protein(s) or peptide(s) in the sample from at least some other components of the sample.

17. The method of claim 11, wherein the first electrode is an anode (positive charge) and the second electrode is a cathode (negative charge), and the controlling comprises adjusting the pH of the fluid above the pI of the target protein(s) or peptide(s) such that the target protein(s) or peptide(s) have an overall negative charge and at least some other components of the sample are positively-charged; and the applying results in movement of the positively-charged components to the second sub-chamber and the target protein(s) or peptide(s) remain in the first sub-chamber; and removing fluid comprising the moved components from the second sub-chamber and optionally replacing the removed fluid with new fluid in the second sub-chamber; and subsequently controlling the injector/extractors to adjust the pH of the fluid in the chamber to a pH below the pI of the target protein(s) or peptide(s) such that the target protein(s) or peptide(s) have an overall positive charge;

applying a voltage between the first and second electrode, thereby moving the positively-charged target protein(s) or peptide(s) into the second sub-chamber; and removing and collecting the fluid in the second chamber, including the target protein(s) or peptide(s), via the outlet in the second sub-chamber, thereby separating the target protein(s) or peptide(s) in the sample from at least some other components of the sample.

18. The method of claim 11, wherein the sample comprises proteins and the dividing membrane contains pores that allow passage of peptides smaller than a molecular cut-off but that substantially block passage of peptides larger than the cut-off, and the loading comprises loading the sample into the first sub-chamber, optionally, the controlling comprises controlling the injector/extractors to adjust the pH of the fluid in the first sub-chamber;

adding a first protease to the first-sub chamber under conditions to allow the first protease to generate peptides from the proteins;

applying a voltage between the first and second electrode, thereby moving at least some charged peptides having a size below the molecular cut-off into the second sub-chamber.

19. The method of claim 18, wherein the molecular cut-off is about 10, 15, 20, 25, or 30 kDa.

20. The method of claim 18, further comprising, adding a second protease to the first sub-chamber under conditions to allow the second protease to generate peptides from the proteins;

applying a voltage between the first and second electrode, thereby moving at least some charged peptides having a size below the molecular cut-off into the second sub-chamber.

21. The method of claim 20, comprising, before or after adding the second protease, adjusting the pH of the fluid in the first sub-chamber to a pH optimized for the second protease.

22. The method of claim 18, wherein before the adding of the first protease, the method comprises applying a voltage between the first and second electrode, thereby moving at least some charged peptides, if present from the sample, into the second sub-chamber.

23. The method of claim 18, further comprising collecting the peptides in the second sub-chamber.

* * * * *